US012697020B2

(12) United States Patent

Hause et al.

(10) Patent No.: US 12,697,020 B2

(45) Date of Patent: Aug. 4, 2026

(54) VIDEO LARYNGOSCOPE IMAGE FILE MANAGEMENT SYSTEMS AND METHODS

(71) Applicant: Covidien LP, Mansfield, MA (US)

(72) Inventors: Alexandra R. Hause, Boulder, CO (US); Natalie I. Jagelski, Lafayette, CO (US); Robert W. Eikel, Lafayette, CO (US); Derek Scot Tata, Longmont, CO (US); Peter Douglas Colin Inglis, Boulder, CO (US); Nicholas Robertson, Erie, CO (US); Brittany W. Armstrong, Louisville, CO (US)

(73) Assignee: Covidien LP, Mansfield, MA (US)

( * ) Notice: Subject to any disclaimer, the term of this patent is extended or adjusted under 35 U.S.C. 154(b) by 380 days.

(21) Appl. No.: 18/047,426

(22) Filed: Oct. 18, 2022

(65) Prior Publication Data

US 2023/0124915 A1 Apr. 20, 2023

Related U.S. Application Data

(60) Provisional application No. 63/257,895, filed on Oct. 20, 2021.

(51) Int. Cl.
    *A61B 1/267*     (2006.01)
    *A61B 1/00*     (2006.01)
    (Continued)

(52) U.S. Cl.
    CPC .......... *A61B 1/267* (2013.01); *A61B 1/00016* (2013.01); *A61B 1/0002* (2013.01); *A61B 1/0004* (2022.02); *A61B 1/00052* (2013.01);
    *A61B 1/04* (2013.01); *G06F 3/04817* (2013.01); *G06F 16/16* (2019.01); *G06V 10/56* (2022.01);
    (Continued)

(58) Field of Classification Search
    CPC ........................................ A61B 1/267–1/2676
    See application file for complete search history.

(56) References Cited

U.S. PATENT DOCUMENTS 8,194,122 B2    6/2012   Amling et al.
8,652,033 B2    2/2014   Berci et al.
(Continued)

FOREIGN PATENT DOCUMENTS

EP         2433553 A1    3/2012
GB        2578263 A   *   4/2020      ............. A61B 1/267
(Continued)

OTHER PUBLICATIONS

Ambu_aScope_3_Large_Brochure_4963605 (Oct. 2017).
(Continued)

*Primary Examiner* — Julianna N Harvey

(57) ABSTRACT

A video laryngoscope system acquires images that can, in embodiments, be recorded and stored in a memory of the video laryngoscope. In an embodiment, the video laryngoscope can be operated in an automatic recording mode, and the acquired images are recorded automatically with no further user input and stored in a memory of the video laryngoscope. If the video laryngoscope is paired to a wireless hub, the acquired images are automatically transferred to the wireless hub in response to a power off user input. Other recording modes may use manual inputs to initiate recording and storing of the acquired images.

20 Claims, 23 Drawing Sheets

(51) Int. Cl.

| | | |
|---|---|---|
| *A61B 1/04* | (2006.01) | |
| *G06F 3/04817* | (2022.01) | |
| *G06F 16/16* | (2019.01) | |
| *G06V 10/56* | (2022.01) | |
| *G06V 20/40* | (2022.01) | |
| *H04N 5/77* | (2006.01) | |

(52) U.S. Cl.

CPC .............. *G06V 20/46* (2022.01); *H04N 5/77* (2013.01); *G06V 2201/031* (2022.01)

(56) References Cited

U.S. PATENT DOCUMENTS

| | | | | |
|---|---|---|---|---|
| 8,715,172 | B1 | 5/2014 | Girgis | |
| 8,746,239 | B2 | 6/2014 | Yoshida | |
| 8,827,899 | B2 | 9/2014 | Farr et al. | |
| 8,982,199 | B2 | 3/2015 | Amling et al. | |
| 9,123,155 | B2 | 9/2015 | Cunningham et al. | |
| 9,498,112 | B1 | 11/2016 | Stewart et al. | |
| 9,538,908 | B2 | 1/2017 | Allyn et al. | |
| 9,687,141 | B2 | 6/2017 | McGrath | |
| 9,820,641 | B2 | 11/2017 | McGrath | |
| 10,010,379 | B1 | 7/2018 | Gibby et al. | |
| 10,149,957 | B2 | 12/2018 | Runnels | |
| 10,307,599 | B2 | 6/2019 | Schilling | |
| 11,116,587 | B2 * | 9/2021 | Wolf | A61B 34/10 |
| 2006/0149156 | A1 * | 7/2006 | Cochran | A61B 5/0006 |
| | | | | 600/509 |
| 2007/0106117 | A1 * | 5/2007 | Yokota | A61B 1/042 |
| | | | | 348/E5.025 |
| 2007/0197896 | A1 | 8/2007 | Moll et al. | |
| 2007/0236514 | A1 | 10/2007 | Agusanto et al. | |
| 2008/0177146 | A1 | 7/2008 | Chen | |
| 2008/0177148 | A1 | 7/2008 | Chen et al. | |
| 2008/0312507 | A1 | 12/2008 | Kim | |
| 2011/0130632 | A1 * | 6/2011 | McGrail | A61B 1/267 |
| | | | | 600/188 |
| 2011/0137127 | A1 | 6/2011 | Schwartz | |
| 2011/0245609 | A1 | 10/2011 | Laser | |
| 2012/0046521 | A1 * | 2/2012 | Hunter | A61B 5/061 |
| | | | | 600/104 |
| 2012/0078055 | A1 * | 3/2012 | Berci | A61B 1/267 |
| | | | | 600/188 |
| 2013/0057667 | A1 | 3/2013 | McGrath | |
| 2013/0267838 | A1 | 10/2013 | Fronk et al. | |
| 2014/0031700 | A1 | 1/2014 | Ferrantelli | |
| 2014/0160261 | A1 | 6/2014 | Miller et al. | |
| 2014/0275760 | A1 | 9/2014 | Lee et al. | |
| 2014/0378763 | A1 | 12/2014 | Atarot | |
| 2015/0080655 | A1 * | 3/2015 | Peterson | A61B 1/000095 |
| | | | | 600/112 |
| 2016/0051781 | A1 * | 2/2016 | Isaacs | A61B 1/267 |
| | | | | 600/188 |
| 2016/0199009 | A1 | 7/2016 | Gilboa | |
| 2016/0279365 | A1 | 9/2016 | Esnouf | |
| 2017/0055809 | A1 | 3/2017 | Omoto | |
| 2017/0209071 | A1 | 7/2017 | Zhao et al. | |
| 2017/0258313 | A1 | 9/2017 | McGrath | |
| 2017/0291001 | A1 * | 10/2017 | Rosenblatt | A61B 1/267 |
| 2018/0193102 | A1 | 7/2018 | Inoue | |
| 2018/0292199 | A1 | 10/2018 | Tojo et al. | |
| 2018/0296281 | A1 | 10/2018 | Yeung et al. | |
| 2018/0324352 | A1 | 11/2018 | Furuhata | |
| 2019/0133430 | A1 * | 5/2019 | Inglis | A61B 1/267 |
| 2020/0029793 | A1 | 1/2020 | McGrath | |
| 2020/0195903 | A1 | 6/2020 | Komp et al. | |
| 2020/0275824 | A1 * | 9/2020 | Tata | A61B 1/267 |
| 2020/0367742 | A1 | 11/2020 | McGrath | |
| 2020/0383561 | A1 | 12/2020 | McGrath | |
| 2021/0052140 | A1 | 2/2021 | Tata | |
| 2021/0121155 | A1 | 4/2021 | Maguire | |
| 2021/0127949 | A1 | 5/2021 | Tata | |
| 2021/0128033 | A1 | 5/2021 | Tata | |
| 2021/0137350 | A1 | 5/2021 | Inglis | |
| 2021/0169435 | A1 * | 6/2021 | Nonaka | A61B 6/4233 |
| 2021/0257856 | A1 | 8/2021 | Ng | |
| 2021/0259536 | A1 | 8/2021 | Inglis | |
| 2021/0275008 | A1 | 9/2021 | McGrath | |
| 2021/0318382 | A1 | 10/2021 | McGrath | |
| 2022/0110504 | A1 | 4/2022 | Inglis | |
| 2022/0225859 | A1 | 7/2022 | Phillips | |
| 2022/0257092 | A1 | 8/2022 | Ng | |
| 2022/0354380 | A1 | 11/2022 | Tata | |
| 2023/0029630 | A1 | 2/2023 | Ng | |

FOREIGN PATENT DOCUMENTS

| | | |
|---|---|---|
| JP | 2014210085 A | 11/2014 |
| WO | 2020/005890 A1 | 1/2020 |

OTHER PUBLICATIONS

Mcgrath Mac—Video Laryngoscope Operator's Manual Instructions for Use—Aircraft Medical Ltd (2017) www.aircraftmedical.com—23 pages.

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS ONE | https://doi.org/10.1371/journal.pone.0186691 (Nov. 3, 2017).

* cited by examiner

220

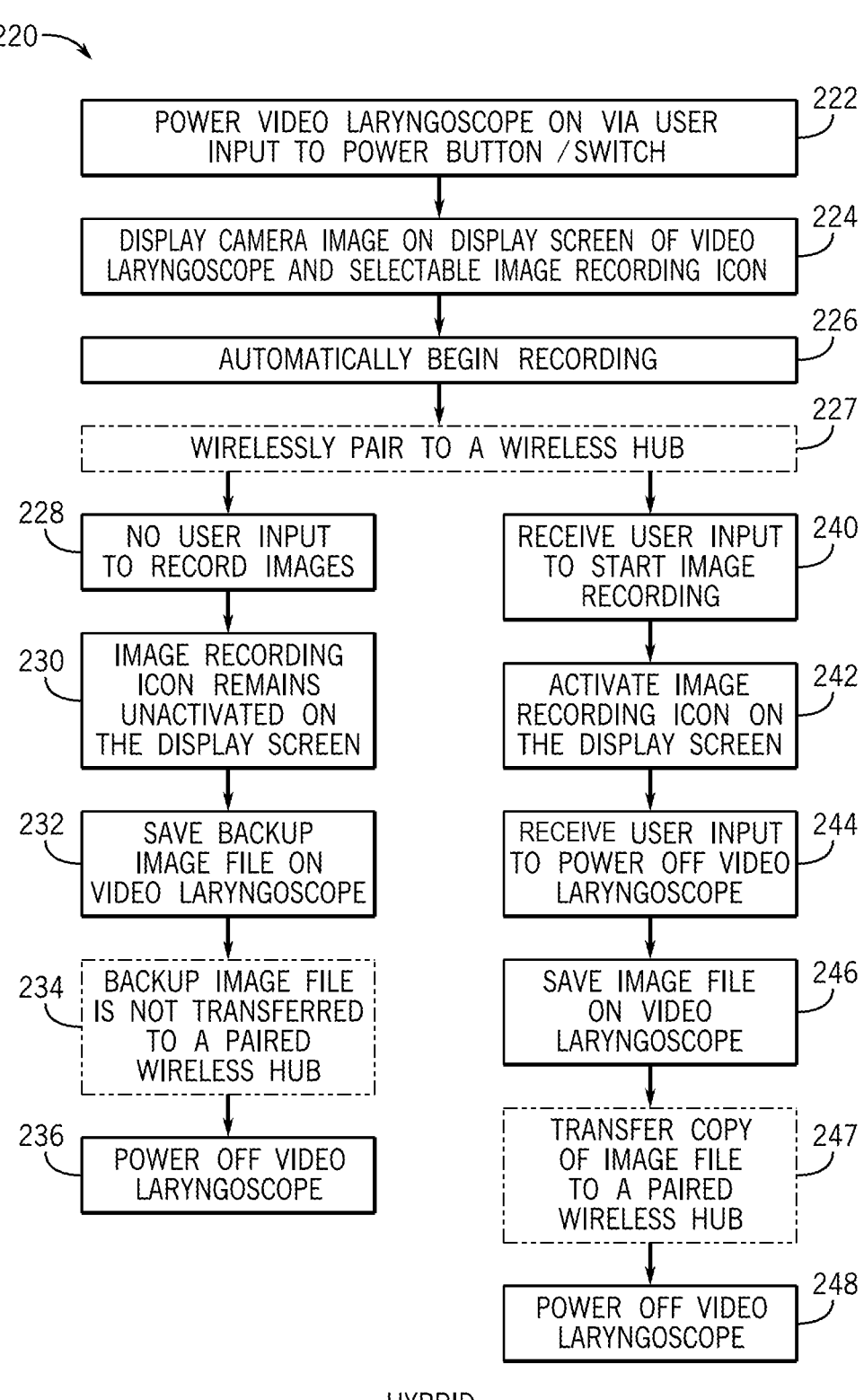

222
POWER VIDEO LARYNGOSCOPE ON VIA USER INPUT TO POWER BUTTON / SWITCH

224
DISPLAY CAMERA IMAGE ON DISPLAY SCREEN OF VIDEO LARYNGOSCOPE AND SELECTABLE IMAGE RECORDING ICON

226
AUTOMATICALLY BEGIN RECORDING

227
WIRELESSLY PAIR TO A WIRELESS HUB

228
NO USER INPUT TO RECORD IMAGES

230
IMAGE RECORDING ICON REMAINS UNACTIVATED ON THE DISPLAY SCREEN

232
SAVE BACKUP IMAGE FILE ON VIDEO LARYNGOSCOPE

234
BACKUP IMAGE FILE IS NOT TRANSFERRED TO A PAIRED WIRELESS HUB

236
POWER OFF VIDEO LARYNGOSCOPE

240
RECEIVE USER INPUT TO START IMAGE RECORDING

242
ACTIVATE IMAGE RECORDING ICON ON THE DISPLAY SCREEN

244
RECEIVE USER INPUT TO POWER OFF VIDEO LARYNGOSCOPE

246
SAVE IMAGE FILE ON VIDEO LARYNGOSCOPE

247
TRANSFER COPY OF IMAGE FILE TO A PAIRED WIRELESS HUB

248
POWER OFF VIDEO LARYNGOSCOPE

HYBRID
RECORDING MODE

FIG. 8

VIDEO LARYNGOSCOPE IMAGE FILE MANAGEMENT SYSTEMS AND METHODS

CROSS-REFERENCE TO RELATED APPLICATIONS

This application claims the benefit of U.S. Provisional Application No. 63/257,895 filed Oct. 20, 2021, entitled "Video Laryngoscope Image file Management Systems and Methods," which is incorporated herein by reference in its entirety.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Laryngoscopes are in common use during intubation (the insertion of an endotracheal tube into the trachea of a patient). The video laryngoscope is a form of indirect laryngoscopy in which a medical professional (such as a doctor, therapist, nurse, or other practitioner) views a video image of the patient's larynx on a display screen. A video laryngoscope may include an integral display that is in the line-of-sight of the laryngoscope operator so that the patient airway is viewable on the display screen in real-time to facilitate navigation and insertion of tracheal tubes within the airway.

SUMMARY

Certain embodiments are summarized below. These embodiments are not intended to limit the scope of the disclosure. Indeed, the present disclosure may encompass a variety of forms that may be similar to or different from the embodiments set forth below.

In one embodiment, a video laryngoscope includes a power switch that powers the video laryngoscope on and off in response to user input. The video laryngoscope also includes a camera that acquires images while the video laryngoscope is powered on; a processor that operates to: record the acquired images; identify one or more characteristics of the acquired airway images; and name the file or a folder containing the file based on the one or more identified characteristics. The video laryngoscope also includes a memory that stores the file of the acquired airway images or the folder using the name.

In one embodiment, a video laryngoscope data review system includes a connection port and first wireless communication circuitry. The system also includes a computer coupled to the wireless hub via a removable cable, wherein the removable cable is inserted into the connection port of the wireless hub to couple to the computer, and the computer includes a display; and a processor. The system also includes a video laryngoscope comprising: a memory storing one or more image files; and second wirelessly communication circuitry that operates to wirelessly pair the video laryngoscope with the wireless hub via communication with the first wireless communication circuitry; wherein, responsive to wireless pairing of the video laryngoscope and the wireless hub, the processor of the computer operates to display the one or more image files on the display of the computer.

In one embodiment, a video laryngoscope image recording method includes the steps of receiving a power on user input at a video laryngoscope; powering on the video laryngoscope in response to the user input, wherein the video laryngoscope is in an automatic recording mode when powered on; acquiring images using a camera of a video laryngoscope in the automatic recording mode; wirelessly pairing to a wireless hub; receiving a power off user input; automatically storing the acquired images in a memory of the video laryngoscope without additional user input; automatically transferring the acquired images to the wireless hub without additional user input; and powering off the video laryngoscope after automatically transferring the acquired images.

In one embodiment, a video laryngoscope image recording method includes the steps of receiving a power on user input at a video laryngoscope; powering on the video laryngoscope in response to the user input, wherein the video laryngoscope is in a manual recording mode when powered on; acquiring images using a camera of a video laryngoscope in the manual recording mode; receiving a recording user input to record the acquired images; wirelessly pairing to a wireless hub; receiving a power off user input; storing the acquired images in a memory of the video laryngoscope based on the user input to record the acquired images; transferring the acquired images to the wireless hub based on the user input to record the acquired images; and powering off the video laryngoscope after transferring the acquired images.

BRIEF DESCRIPTION OF THE DRAWINGS

Advantages of the disclosed techniques may become apparent upon reading the following detailed description and upon reference to the drawings in which:

FIG. 8 is a flow diagram of a method of acquiring images in a hybrid manual-automatic recording mode of a video laryngoscope, in accordance with an embodiment of the present disclosure;

DETAILED DESCRIPTION OF SPECIFIC EMBODIMENTS

Figure 1:
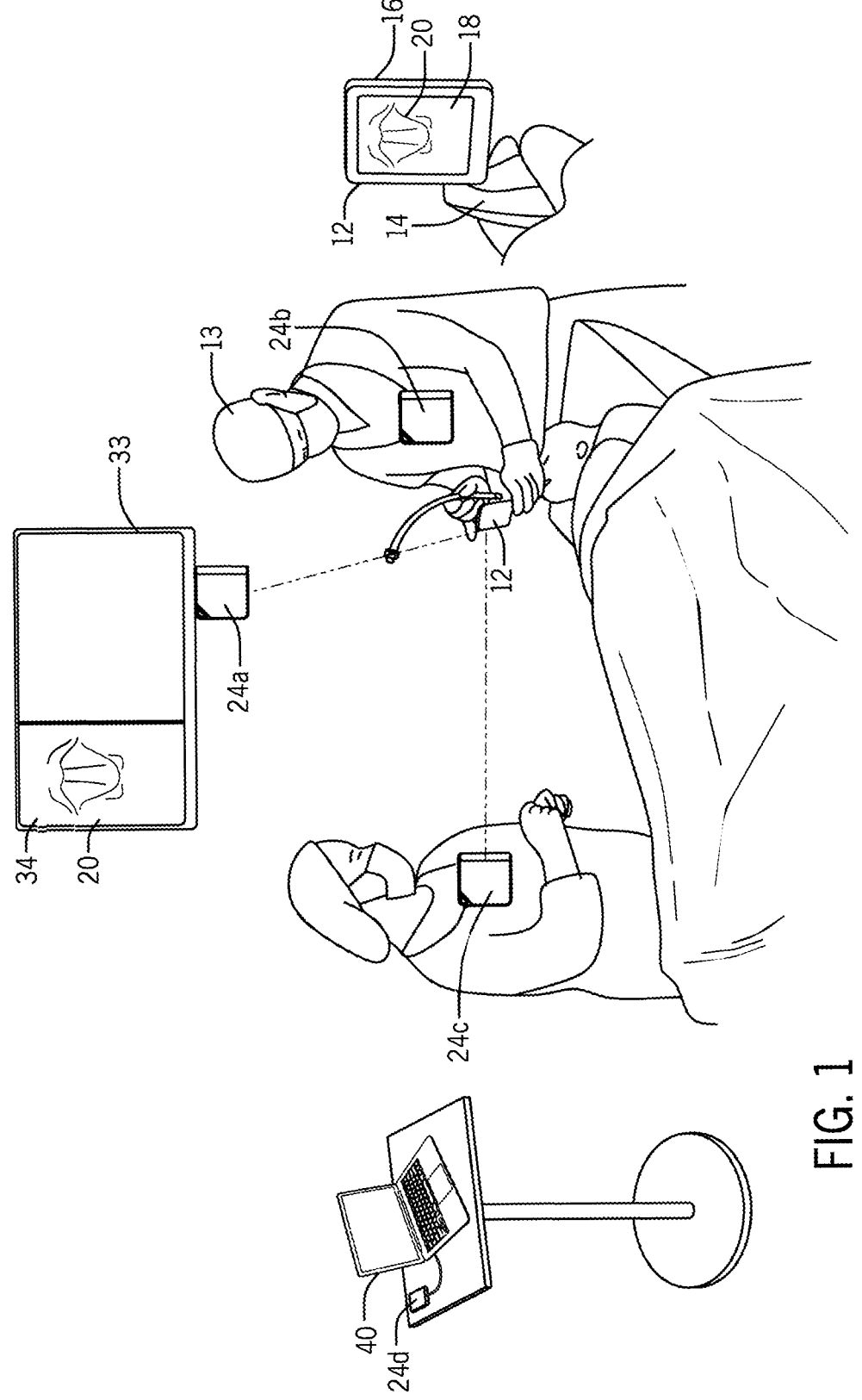
FIG. 1 is a schematic illustration of a patient environment including a video laryngoscope image file management system, in accordance with an embodiment of the present disclosure.

A medical professional may use a laryngoscope to view a patient's oral cavity to facilitate insertion of a tracheal tube (e.g., endotracheal tube, tracheostomy tube, or transtracheal tube) through the patient's oral or nasal cavity and into the patient's trachea as part of an intubation procedure. Video laryngoscopes include a camera on a portion of the laryngoscope that is inserted into the patient's oral cavity to obtain an image (e.g., still image and/or moving image, such as a video) of the oral cavity or airway anatomy, e.g., upper airway anatomy. The image may then be displayed during the intubation procedure to enable the medical professional to visualize the airway and to facilitate manipulation and insertion of the tracheal tube. The images acquired by the video laryngoscope can provide important context to other medical professionals participating in a medical procedure. Accordingly, in some cases, the video laryngoscope can be linked to a relatively larger external display that duplicates the display screen of the video laryngoscope such that other medical professionals can track the progress of the intubation or other airway procedure in real time on the external display.

In some cases, rather than each medical professional having his or her own personal device, video laryngoscopes can be a shared resource, e.g., provided from a hospital or other medical inventory, for use during a medical procedure. After the procedure is complete, the video laryngoscope can be cleaned and returned to the inventory for maintenance and storage until needed again. As a result, over the course of several different medical procedures, a particular video laryngoscope can be used by different medical professionals to acquire videos and/or still images during medical procedures of different patients. In addition, the video laryngoscope can include recording capabilities such that images of each individual procedure can be saved directly to a memory of the video laryngoscope. While video laryngoscopes can directly store acquired images, accessing the images directly from the memory of the video laryngoscope may not be convenient for medical professional wishing to review their past procedures. For example, the video laryngoscope may not support a user-friendly file review interface, and the default naming conventions of the image files stored on the video laryngoscope may not be informative. Thus, a medical professional may need to individually select and review each different stored image file to determine if the associated images are of interest and/or are from his or her own procedures.

Provided herein are video laryngoscope image file management systems that facilitate automatic image recording, manual image recording, or hybrid image recording operating modes for a video laryngoscope. A laryngoscope operator or medical facility administrator can select a desired recording mode of the available operator modes of the video laryngoscope based on whether higher or lower levels of image file retention are desired. The automatic recording mode provides a highest level of file retention and sharing. In the automatic recording mode, the video laryngoscope defaults to automatic recording of all images acquired while the video laryngoscope is operating. Further, the video laryngoscope defaults to automatically transferring the recorded images acquired during operation to a paired portable storage device, e.g., a paired wireless hub. Thus, the video laryngoscope can be used with minimal or no user input to automatically record, and transfer, images. However, some medical professionals may prefer not to retain images files from all cases. A manual image recording mode permits recording and/or automatic transfer of interesting or relevant images on a case-by-case basis. In manual recording mode, the video laryngoscope defaults to no image file recording and retention unless the laryngoscope operator selects or otherwise provides an input to activate image recording during each procedure. When image recording is activated in the manual recording mode, automatic file transfer to a paired wireless hub is also activated. In another embodiment, a hybrid image recording mode automatically records and saves acquired images in a backup folder on a video laryngoscope, but otherwise does not transfer these images to any paired wireless hubs unless a user has provided an input to record the procedure. Thus, the laryngoscope operator can still select image recording, and transfer to a paired wireless hub, on a case-by-case basis. Further, in the event that a case was inadvertently not selected for recording, the associated image files are able to be retrieved from a backup folder. The backup folder can be periodically emptied so that these image files are not permanently stored. Thus, a video laryngoscope as provided herein can receive a user selection of an automatic image recording, a manual image recording, or a hybrid image recording mode and will operate to retain and/or transfer acquired images as a function of the selected recording mode.

Also provided herein are video laryngoscope image file management systems and methods that use user flags and/or image characteristics of the acquired images of the video laryngoscope to name or organize video laryngoscope image files that are stored on the memory of the video laryngoscope and/or video laryngoscope image files that are communicated to separate devices, such wireless hubs or computers. Further, the video laryngoscope image file management systems and methods can include providing an image repository retained on the video laryngoscope from which recorded laryngoscope images can be retrieved days or weeks after the images are recorded.

The disclosed embodiments of the video laryngoscope image file management system can be used in conjunction with a video laryngoscope system 10, illustrated in a patient environment in FIG. 1. The patient environment can be any room where an intubation is being performed, such as a medical suite in a hospital or other care setting, an operating or other procedure room, patient recovery room, an emergency intubation setting, or other environments. The video laryngoscope system 10 can include a video laryngoscope 12 that, in operation, is used for airway visualization of a patient. The video laryngoscope system 10 may additionally or alternatively be used with other patient visualization instruments that acquire patient images, e.g., internal patient images.

A laryngoscope operator 13 holds a handle 14 of the laryngoscope coupled to a display portion 16 having a display screen 18. Acquired images 20 are displayed on the display screen 18. The video laryngoscope 12 may be used as part of an intubation procedure to advance a tracheal tube into a patient airway to secure the airway for mechanical ventilation. Accordingly, the operator 13 of the video laryngoscope 12 performs the intubation and directly manipulates the endotracheal tube within the patient's airway, and other clinicians in the patient environment assist the laryngoscope operator, monitor a condition of the patient, prepare or adjust medical equipment in the patient environment, and/or wait until the airway is secured to perform other procedures or interventions. As provided herein, the images 20 can be stored in a memory on the video laryngoscope 12. The images 20 acquired by the video laryngoscope 12 are visible on the laryngoscope display screen 18 that is positioned in the operator's line of sight.

FIG. 1 illustrates arrangements of the system 10 using wireless hubs 24. A wireless hub 24, as provided herein, may be implemented as a puck, wand, dongle, module, or disc having a housing 50 that can be sized and shaped to be portable and, in embodiments, handheld or lightweight. The wireless hub 24 can be housed separately from coupled or paired devices. The wireless hub 24 may be multifunctional or capable of operating in one of a plurality of operating modes. Notably, each illustrated wireless hub 24 can be a same type of device that is operating differently based on a pairing arrangement of the wireless hub 24 with other devices. In one arrangement, a wireless hub 24a in a streaming operating mode is coupled to an external display 33 and is also wirelessly paired to the video laryngoscope 12. The acquired images 20 from the video laryngoscope 12 are streamed from the video laryngoscope 12 to the wireless hub 24a and provided from the wireless hub 24a to the external display 33 for display on all or a portion of an external display screen 34. Thus, in an embodiment, the images 20 displayed on the laryngoscope display screen 18 and streamed to the external display screen 34 are substantially the same real-time images. In the illustrated embodiment, the wireless hub 24a is directly coupled to an input port of the external display 33. However, other coupling arrangements (e.g., wireless, wired) are also contemplated.

The system 10 can additionally or alternatively include wireless hubs 24b, 24c in a data transfer operating mode that are wirelessly paired to the video laryngoscope 12, are not coupled to the external display 33, and that are operating as personal data storage devices to receive images 20. Thus, the wireless hubs 24b, 24c are paired only to the video laryngoscope 12, and not to any other devices, in the data transfer operating mode. In the illustrated example, the wireless hubs 24b, 24c are worn on lanyards by different medical professionals participating in the medical procedure and who wish to receive the images 20. However, the wireless hubs 24b, 24c can be carried or worn by medical professionals in other arrangements (e.g., clipped to a gown, carried in a pocket). Further, the patient environment may include dedicated locations on a patient bed or other fixtures in the room that can receive wireless hubs 24 operating in the data transfer operating mode. As discussed herein, pairing of the wireless hub 24 to the video laryngoscope 12 includes an optical transmission and detection to initiate wireless pairing. Thus, the wireless hub 24 can be positioned with an uninterrupted optical path to the video laryngoscope 12 during pairing. Once wirelessly paired, the wireless hub 24 can be positioned under sterile gowns or in a sterile pocket or pouch through which wireless signals are able to pass.

FIG. 1 also illustrates an additional data review operating mode of a wireless hub 24d in which the wireless hub 24d is coupled a computer 40. The computer 40 can be a personal computer, a laptop, a tablet (e.g. a tablet coupled to a portable stand), a multi-parameter patient monitor, a multi-functional medical device or instrument, a networked computer outside of the room, a mobile device, a cloud computing device in communication with a graphical user interface on a device local to an operator, or other device. When the wireless hub 24d is coupled to the computer 40, files containing the images 20 that are stored in a memory of the wireless hub 24d can be viewed and accessed. In the illustrated embodiment, the wireless hub 24 does not contain any integral display, and the computer 40 provides the user interface for interacting with the stored images 20. In the data review operating mode, a medical professional can review videos or still images past medical procedures as part of updating a medical record for a patient. In an embodiment, the wireless hub 24d is not wirelessly paired to any video laryngoscope 12 in the data review operating mode. However, in certain cases, the wireless hub 24d can simultaneously wirelessly pair to the video laryngoscope 12 and also connect to the computer 40 at the same time for a bulk review, access, and/or transfer of files from the video laryngoscope 12 through the wireless hub 24d to the computer 40. In an embodiment, the video laryngoscope 12, when paired to the wireless hub 24d in the data review operating mode, cannot also pair to any other wireless hubs 24 in streaming operating mode, data transfer operating mode, and/or data review operating mode.

Figure 2:
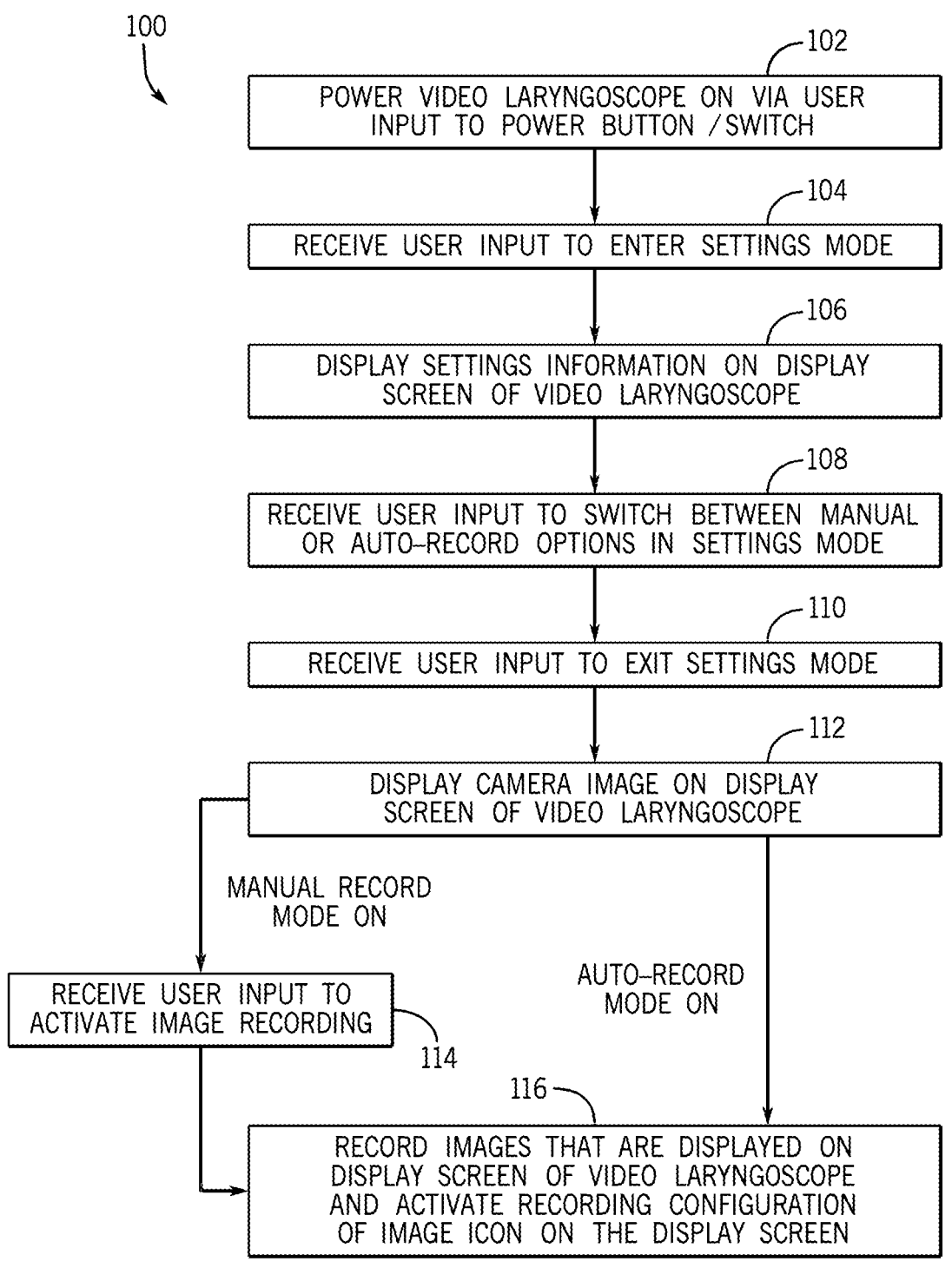
FIG. 2 is a flow diagram of a method of selecting image recording settings of a video laryngoscope, in accordance with an embodiment of the present disclosure.

The video laryngoscope 12 can operate in a particular recording operating mode depending on the selected settings of the video laryngoscope 12. FIG. 2 is a process flow diagram of a method 100 of setting an operating mode of the video laryngoscope 12 with reference to features discussed in FIG. 1, in accordance with an embodiment of the present disclosure. All or some of the method 100 may be performed by a controller of the video laryngoscope 12 and, in some cases, in response to one or more received user inputs. The video laryngoscope 12 powers on in response to a user input (block 102) and can enter a settings mode in response to an additional user input (block 104). The settings mode includes selectable options that are displayed on the laryngoscope display 18 (block 106). In one example, the settings mode includes at least options to select between a manual or automatic (auto-record) recording mode (block 108). In an embodiment, the settings mode additionally or alternatively includes a hybrid or semi-automatic recording mode (see FIG. 3) in which laryngoscope images are retained in a backup folder of the video laryngoscope 12. Subsequent to a user input to exit the settings mode (block 110), the video laryngoscope can return to a default display of the camera image on the laryngoscope display 18 (block 112).

If the video laryngoscope 12 is determined to have a manual recording mode selected, when a user input to activate image recording is received (block 114), the acquired images are recorded (block 116). In an embodiment, an image recording icon is activated to provide an indication to the laryngoscope operator of active recording.

The user input can be a selectable soft key or icon associated with a sensor on the laryngoscope display 18, a button or switch on a body of the video laryngoscope 12, or a gesture-based command (e.g., a movement of the laryngoscope body in a particular pattern). In contrast, if a controller of the video laryngoscope 12 determines that the video laryngoscope 12 is in an automatic recording mode, the acquired images are automatically recorded without further user input after selecting the auto-recording option in the settings of the video laryngoscope 12. In manual recording mode, the image recording includes images acquired only after activation or selection of the image recording user input. In an embodiment, the video laryngoscope 12 can operate in a default mode (e.g., manual or automatic recording), such that, even if the operating mode is changed during operation, the video laryngoscope 12 returns to operating in the default mode at the next power on cycle. In another embodiment, the video laryngoscope 12 retains the settings of the most recently-selected recording mode.

Figure 3:
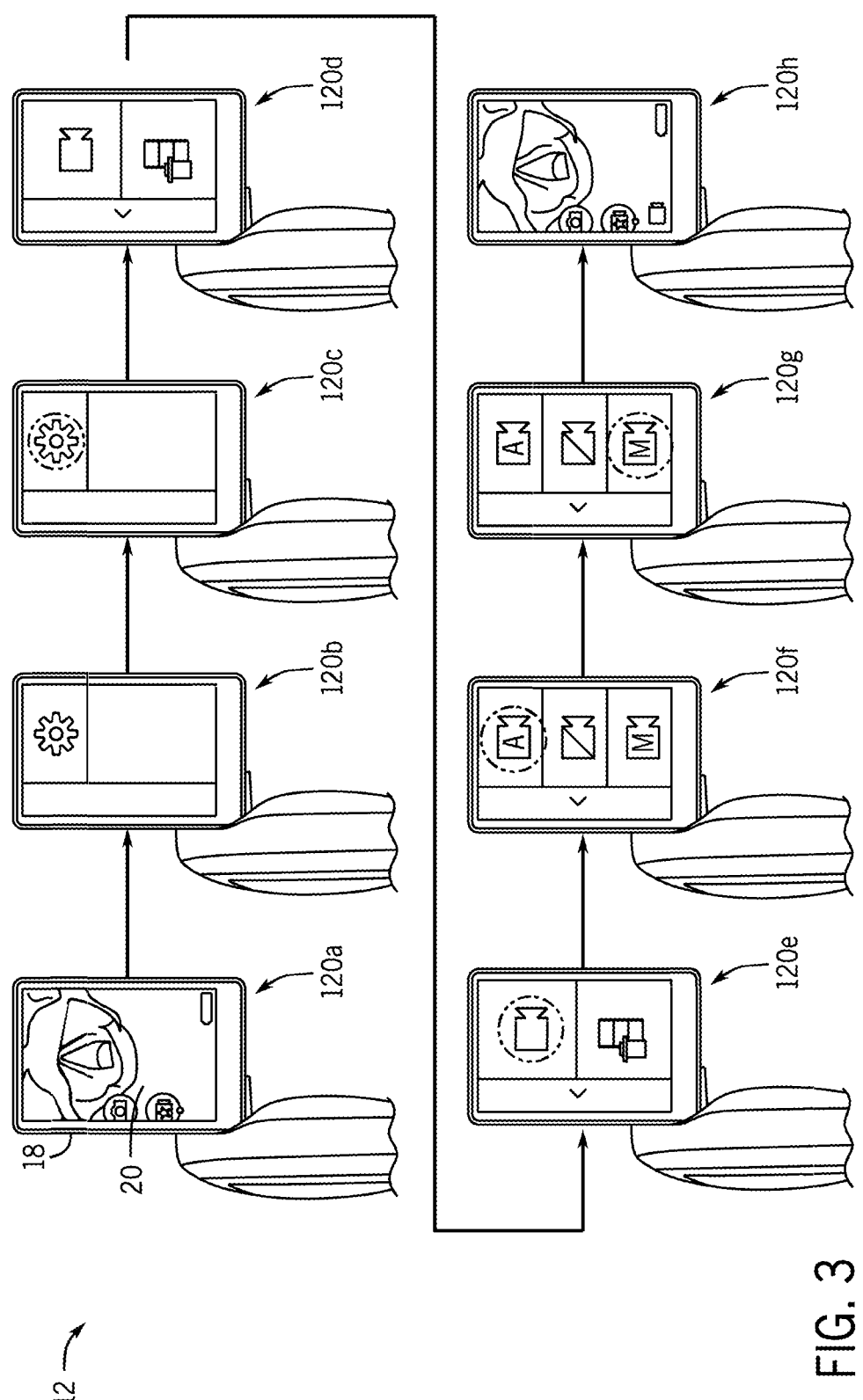
FIG. 3 shows example settings screens in accordance with an embodiment of the present disclosure.

FIG. 3 shows example displays 120 on the display screen 18 of the video laryngoscope 12. Display 120a shows the acquired images 20 that are acquired by the laryngoscope camera in real time. The operator can transition to one or more options screens, such as a menu screen 120b, that can be accessed by a depression of a power button for at least a threshold time, e.g., 10 seconds or longer. Selecting a setting option, as shown on screen 120c, brings up a settings menu screen 120d. In the illustrated example, an upper icon to select a recording mode provides different recording mode settings (screen 120O, and a lower icon provides options to delete retained recordings, e.g., bulk deletion or individual file selection. As shown in 120f, in an embodiment, three different user-selectable recording settings are presented: automatic recording, hybrid or semi-manual recording, and manual recording. In the screen 120f, the automatic recording option is highlighted, indicating that a current recording mode of the video laryngoscope 12 is automatic recording mode.

The illustrated example shows different video icons to distinguish between the three options. In one embodiment, the automatic recording setting can be designated with a filled video icon and/or with "AUTO" or "A" text. The hybrid recording setting can be a half-filled video icon, and the manual recording setting can be designed by an unfilled video icon or with "MANUAL" or "M" text. It should be understood that the illustrated icons representing the available settings are by way of example, and other visual or audio option presentations are also contemplated. For example, the manual recording option is selected in screen 120g to switch the video laryngoscope recording mode to a manual recording mode in which image recording is activated in response to user input. Exiting the options screens, e.g., by a second long depression of the power button, returns the video laryngoscope display 18 to the image screen 120h. However, the user-selected switch from automatic to manual, as shown in screens 120f and 120g, causes the image screen to display a different selection of user input icons. In the illustrated embodiment, the manual mode in screen 120h includes the image recording icon (lower left), while the automatic recording mode image screen 120a does not include the image recording icon. In an embodiment, in the automatic recording mode, the video laryngoscope 12 is always recording without additional user input. Thus, no image recording icon is displayed.

In certain embodiments, the recording mode setting may be based on institutional preferences, such that all available video laryngoscopes 12 for a particular medical environment use a same recording mode. In another embodiment, the recording mode setting is based on the preferences of the laryngoscope operator, who can access the settings to select his or her preferred recording mode.

Figure 4:
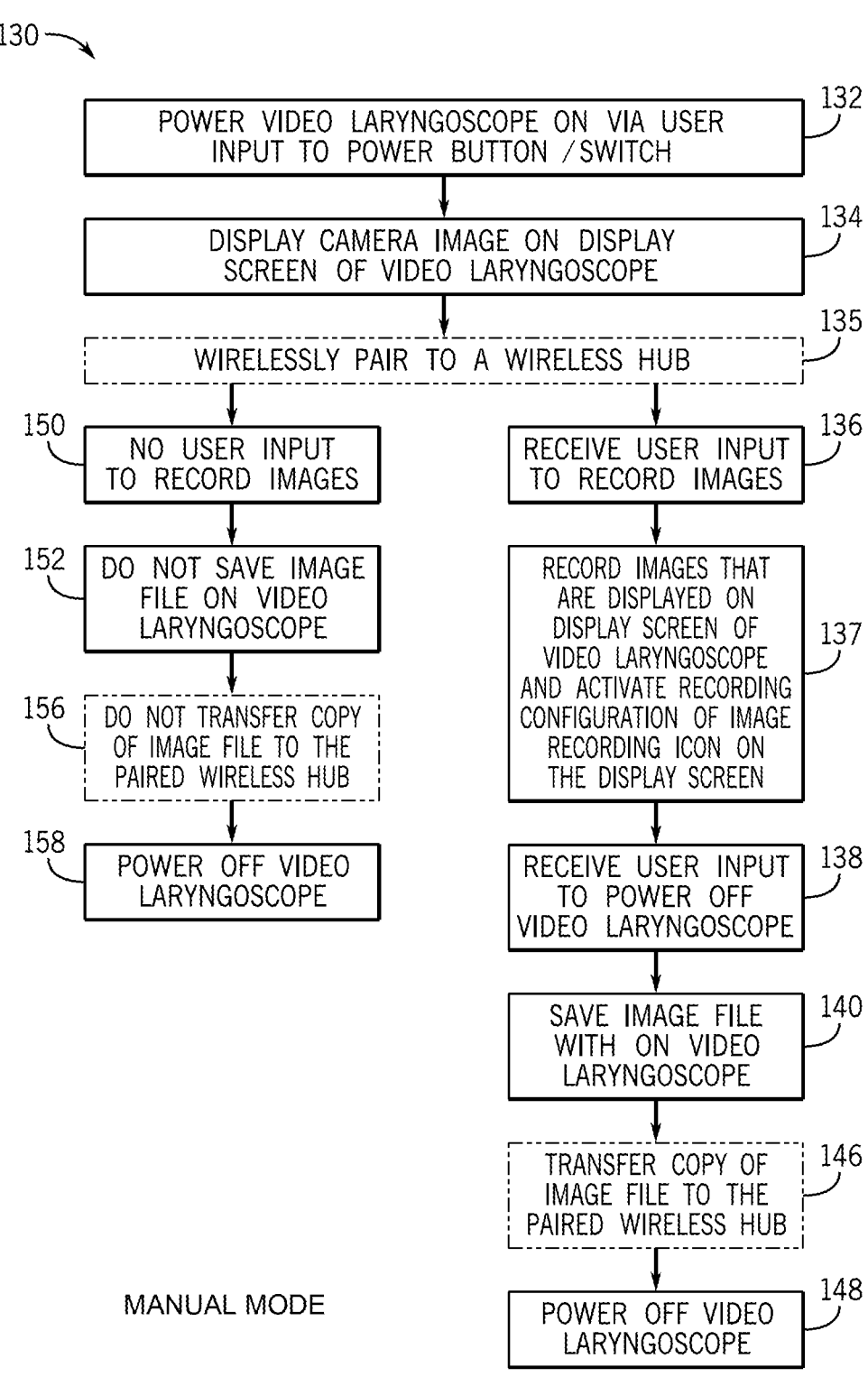
FIG. 4 is a flow diagram of a method of acquiring images in a manual recording mode of a video laryngoscope, in accordance with an embodiment of the present disclosure.

The selected recording mode of the video laryngoscope provides control parameters for conditions for file retention on the video laryngoscope as well as file transfer to a paired wireless hub. FIG. 4 is a process flow diagram of a method 130 of recording images using a manual recording mode of the video laryngoscope 12 with reference to features discussed in FIGS. 1-3, in accordance with an embodiment of the present disclosure. The video laryngoscope 12 powers on in response to a user input (block 132) and acquires images using a camera that are displayed on a display screen 18 of the video laryngoscope (block 134). In embodiments, the video laryngoscope 12 can, optionally, be paired to one or more wireless hubs 24 (block 135).

In the manual recording mode, image recording is initiated only in response to a user input, such as a detected button press or touch command on the display screen 18. In response to receiving a user input to record images (block 136), the video laryngoscope initiates recording mode to retain a recording of the acquired images (block 137). In embodiments, a video recording icon can be displayed or highlighted on the display screen 18 to indicate that recording is active. The recorded images are stored and maintained locally on the video laryngoscope 12. Before powering off in response to receiving a user input to power off the video laryngoscope 12 (block 138), the video laryngoscope 12 saves an image file locally (block 140) that includes acquired.

When the record button or other user input is pressed, the video from the entire power on cycle may be saved (and transferred to a coupled storage device). Because interesting clinical moments may require complete focus, it may not be until after such an event that the operator realizes they want a recording of the procedure. Thus, in an embodiment, the record user input may result in retention of images from a time of power on acquired and before the recording input was provided. In an embodiment, the image file may exclude images acquired by the video laryngoscope 12 before the image recording was initiated. The images that are part of the saved image file are also transferred (e.g., batch transferred) to any paired wireless hub 24 in the data transfer state (block 146) before the video laryngoscope 12 is powered off (block 148). The image transfer to the paired wireless hub 24 occurs automatically in the case of recorded images in the manual recording mode. That is, the user provides input at the video laryngoscope 12 to record images and, when a wireless hub 24 in the data transfer state is paired at the time of power off, no further user input is required to initiate and/or complete the transfer of images to the wireless hub.

The image recording may, in an embodiment, have been active up until and at the time of power off to trigger local saving of the image file and data transfer. In another embodiment, the image recording may not be active at the time of power off such that no image recording is occurring when the power off user input is received. For example, a user may provide a second user input to deactivate image recording at some point during the procedure. However, a state of active image recording at any point during a power on cycle of the video laryngoscope 12 will cause local saving of an image file including images acquired only during a time window of active image recording and automatic transfer of the images acquired during the time window of active image recording in response to the power off user input.

In the manual recording mode, when there is no user input to record images (block 150), the video laryngoscope defaults to not recording the acquired images. In the manual recording mode, when the power off user input is received (block 152), the video laryngoscope 12 does not store or retain an image file of the acquired images (block 154). Further, in the manual recording mode, no image transfer occurs when there is no user input to record the images (block 156). Thus, the video laryngoscope is powered off in response to the power off user input (block 158) without intervening data transfer or data storage steps. Accordingly, in manual recording mode, if the operator does not provide any user input to record images acquired during the power on cycle of the video laryngoscope 12, the images are neither retained in a saved file on the video laryngoscope nor transferred to a paired wireless hub 24 (when present).

Figure 5:
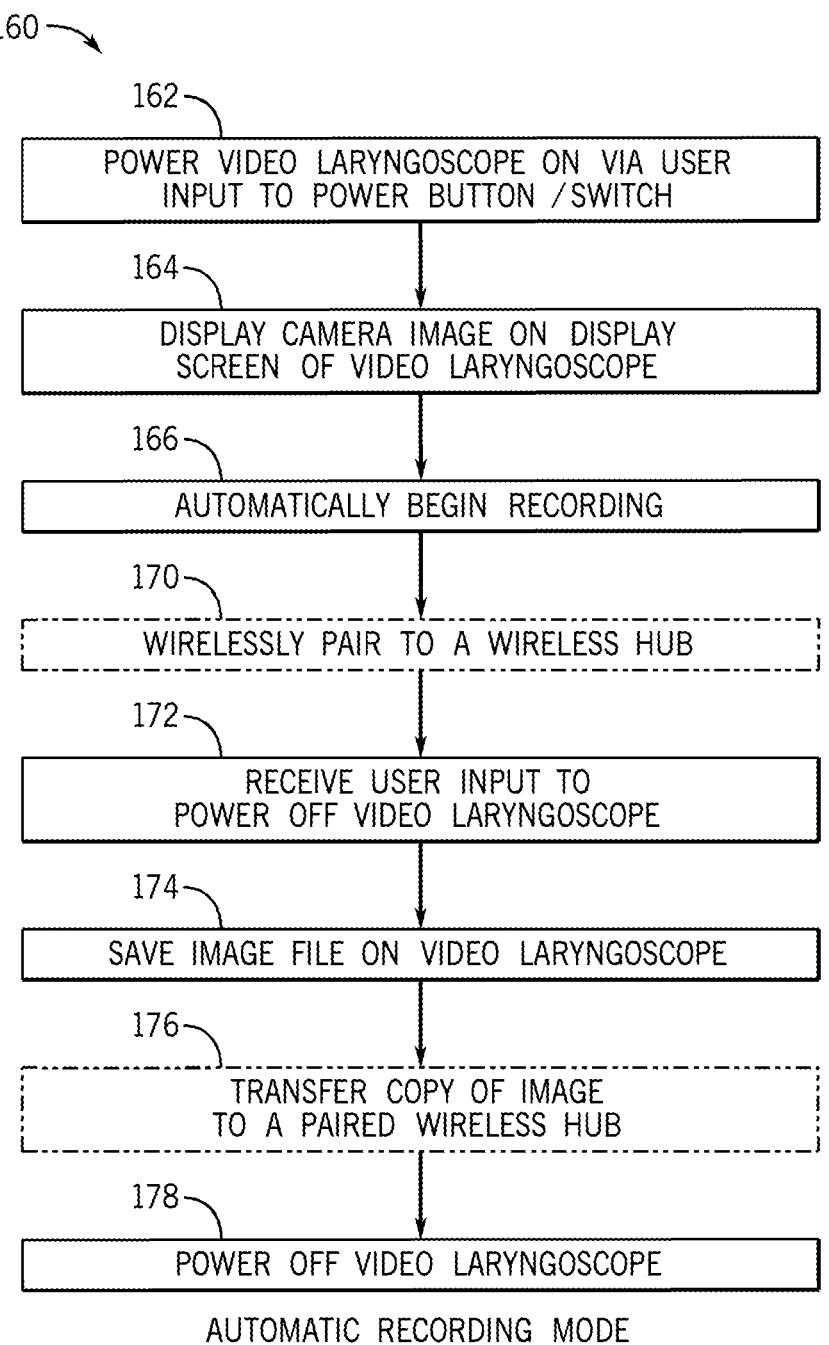
FIG. 5 is a flow diagram of a method of acquiring images in an automatic recording mode of a video laryngoscope, in accordance with an embodiment of the present disclosure.

FIG. 5 is a process flow diagram of a method 160 of recording images using an automatic recording mode of the video laryngoscope 12 with reference to features discussed in FIGS. 1-3, in accordance with an embodiment of the present disclosure. The video laryngoscope 12 powers on in response to a user input (block 162) and acquires images using a camera that are displayed on a display screen 18 of the video laryngoscope (block 164). Concurrently with acquiring and displaying images, the video laryngoscope 12 also automatically initiates recording the acquired images (block 166). In an embodiment, the automatic recording occurs as a background operation, and no image recording icon or other indication of active image recording is activated. In another embodiment, the automatic initiation of image recording also activates display of an image recording icon that provides a visual indication of image recording. Optionally, the video laryngoscope 12 is paired to a wireless hub 24 (block 170).

In the automatic recording mode, image recording is automatically initiated at power on, such that all images acquired while the video laryngoscope 12 is powered on in a power on cycle are automatically recorded without requiring any further user input. At the end of the power on cycle, before powering off in response to a user input to power off the video laryngoscope 12 (block 172), the acquired images are saved to an image file that is retained locally on the video laryngoscope 12 (block 174) and, when the video laryngoscope 12 is paired to a wireless hub 24 at the time the power off user input is received, the acquired images that are saved to the image file are also transferred to the wireless hub 24 (block 176) before the video laryngoscope 12 is powered off (block 178). If there is no paired wireless hub 24, the video laryngoscope 12 powers off without transferring any images.

In an embodiment, the automatic recording mode may automatically initiate recording only after certain internal anatomical features are identified in the acquired images. For example, using the identification of oral cavity features (airway opening, upper airway passage) in the acquired images as a trigger for automatic recording may prevent inadvertent capture of patient or clinician faces in the recording to preserve privacy. Such image feature identification may occur using image identification algorithms (e.g., a feature model) operating on the processor of the laryngoscope 12. Thus, rather than relying on post-recording file editing for privacy, the automatic recording mode (or other recording modes discussed herein) may include security features that prevent patients or caregivers from being in the image recordings, which may improve file security and medical privacy.

In manual recording mode, images can be recorded, and—when recorded-automatically transferred to a paired wireless hub 24, in response to user input to initiate image recording. In contrast, in an automatic recording mode, images are recorded and transferred to a paired wireless hub 24 without requiring any user input that initiates image recording. Further, while manually recorded images may only include a subset of images acquired during a power on cycle of the video laryngoscope 12, depending on when the user input to initiate recording is received, automatically recorded images in automatic recording mode include all of the images acquired over the course of the power on cycle (i.e., the time window between a power on and power off) of the video laryngoscope 12.

Figure 6:
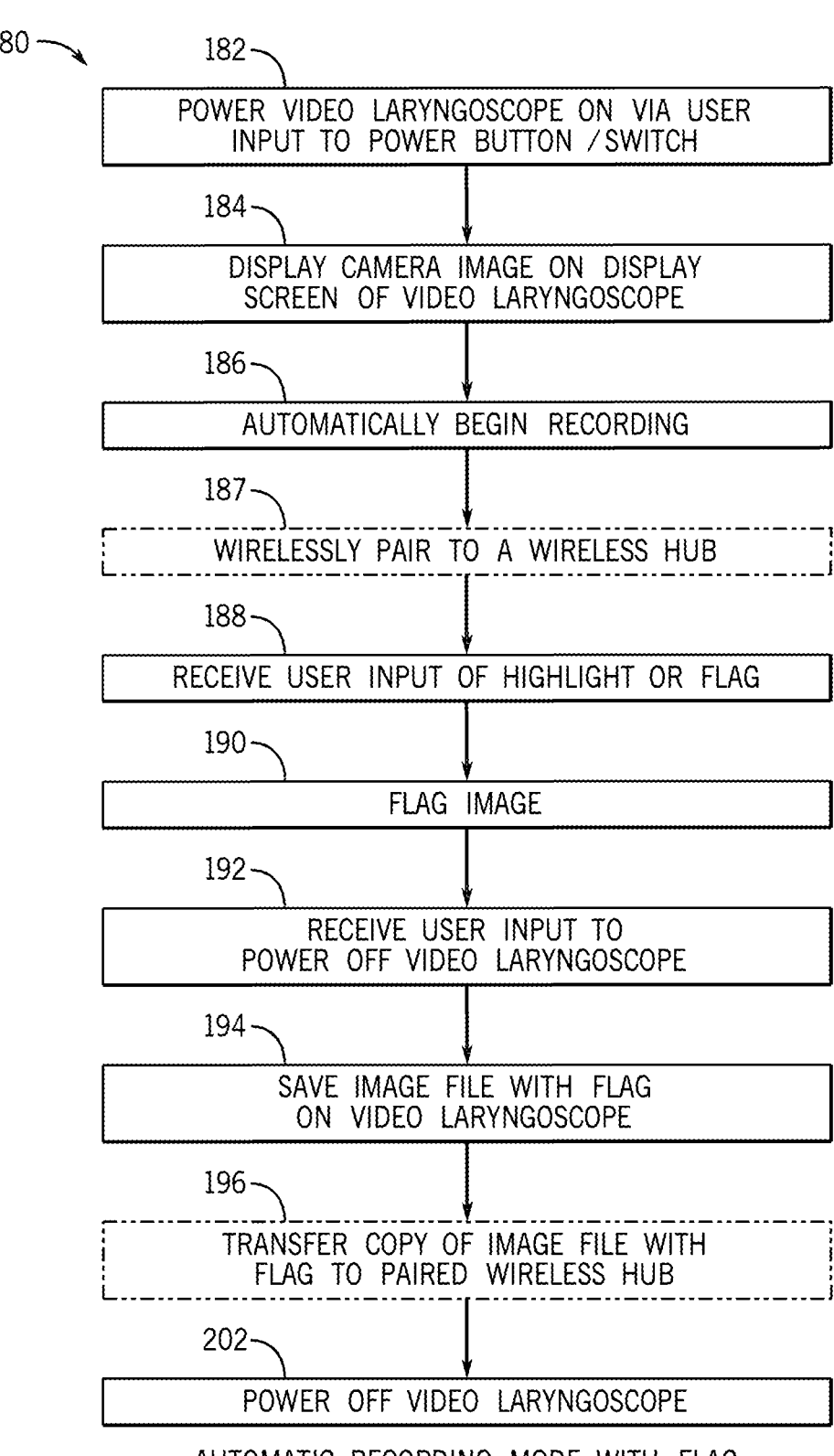
FIG. 6 is a flow diagram of a method of flagging images acquired by a video laryngoscope, in accordance with an embodiment of the present disclosure.

FIG. 6 is a process flow diagram of a method 180 of flagging images during an automatic recording mode of the video laryngoscope 12 with reference to features discussed in FIGS. 1-3, in accordance with an embodiment of the present disclosure. The video laryngoscope 12 powers on in response to a user input (block 182) and acquires images using a camera that are displayed on a display screen 18 of the video laryngoscope (block 184). Concurrently with acquiring and displaying images, the video laryngoscope 12 also automatically initiates recording the acquired images (block 186). Optionally, the video laryngoscope 12 is paired to a wireless hub 24 (block 187).

While the automatic recording mode does not require any user input to initiate recording, the operator can flag or highlight all or some of the recorded images. When a user input of a highlight or flag is received (block 188), one or more of the recorded images is flagged (block 190). In an embodiment, the image correlated with the time of the flag user input is flagged. In an embodiment, the flag is applied to the entire set of images during the power on cycle. At the end of the power on cycle, in response to a user input to power off the video laryngoscope 12 (block 192), the acquired images including the flag are saved to an image file that is retained locally on the video laryngoscope 12 (block 194) and, when the video laryngoscope 12 is paired to a wireless hub 24 at the time the power off user input is received, the acquired images, including the flag, that are saved to the image file are also transferred to the wireless hub 24 (block 196) before the video laryngoscope 12 is powered off (block 202). If there is no paired wireless hub 24, the video laryngoscope 12 powers off without transferring any images.

The presence of the flag can cause the saved image file to be prioritized. For example, the video laryngoscope 12 may retain saved image files according to preset rules (e.g., only retain saved files with no flag that are less than five days old, retain all flagged files indefinitely). The flag can cause the image file to be listed first in a file navigation screen. The flag may be used in a naming convention of the file, such that an operator can identify which files are flagged. While the illustrated flow diagram shows that a flag can be added in an automatic recording mode, a flag user input option may be available in other recording modes as generally discussed herein.

FIGS. 7A-H show an example display screens 18 of a video laryngoscope 12 that displays the acquired images 20 and one or more icons overlaid on the image 20 that may provide operating information and/or selectable options.

Figure 7A:
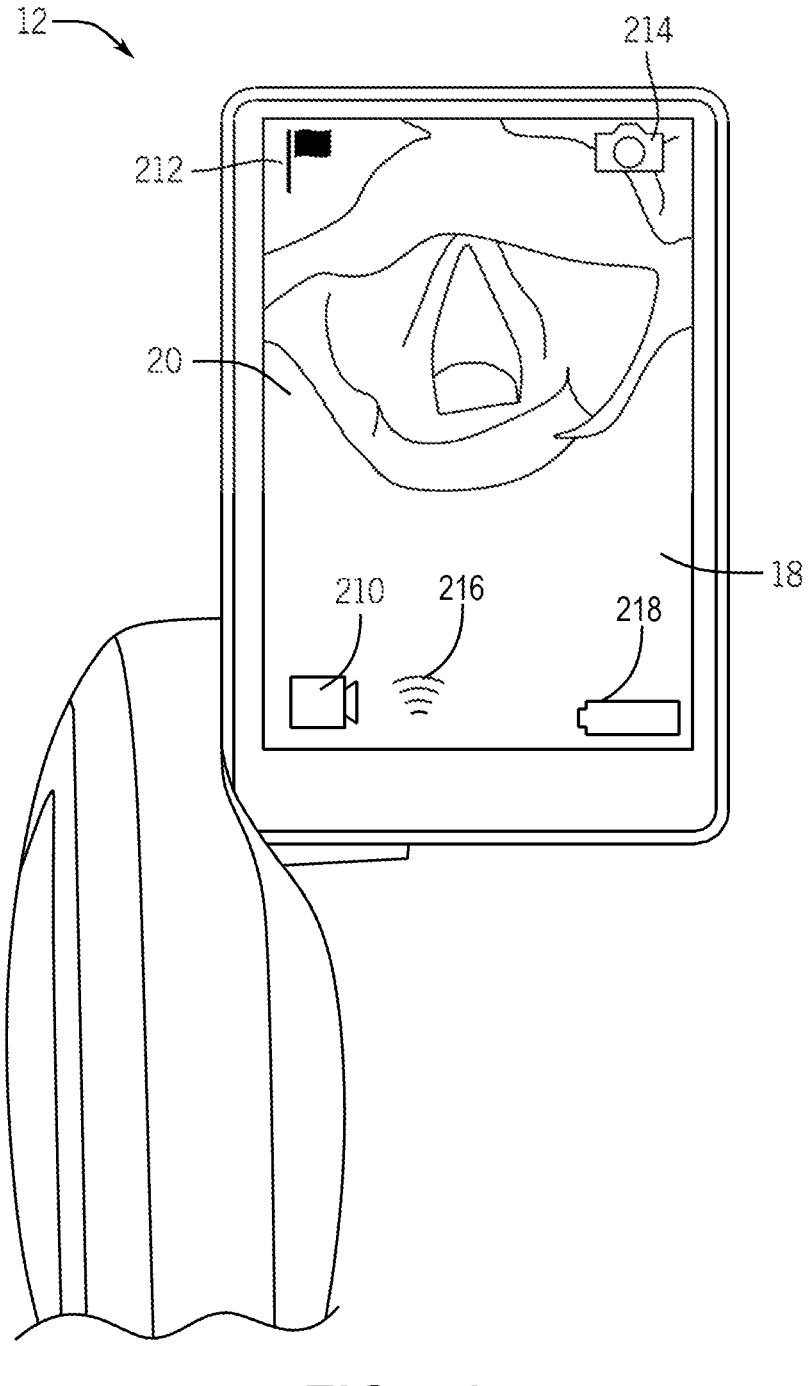
FIGS. 7A-H depict example display screens of a video laryngoscope showing image flagging and recording user input keys, in accordance with an embodiment of the present disclosure.

FIG. 7A depicts an example display screen 18 of a video laryngoscope 12 that displays the acquired images along with an image recording icon 210, a flag icon 212, a wireless connectivity indicator 216, and a battery level indicator 218. Display and selection options of the icons may be controlled by the recording state of the video laryngoscope 12. For example, when the video laryngoscope 12 is in a manual recording mode, the image recording icon 210 may be a selectable icon that, when touched, activates image recording. Activation of the image recording icon 210 may change a configuration of the icon 210 (e.g., a size, shape, color, or fill state) to indicate that the image recording is active. The image recording icon 210 can also be deselected to turn off image recording in a manual recording state. When deselected, the configuration of the image recording icon 210 returns to an inactive state. In contrast, in an automatic recording mode, the image recording icon 210 may not be selectable, so that the operator cannot turn off image recording from the image display screen. Instead, the operator may enter the settings menu (see FIG. 3) to turn off automatic recording. In one example, the image recording icon 210 is displayed in an active configuration in an automatic recording mode or is not displayed at all.

A selectable flag icon 212 can be provided on the display screen 18 that is activated to flag a particular procedure or individual images from the procedure. For example, in an embodiment, a touch input on the flag icon 212 can change a configuration of the flag icon 212 to indicate that the procedure is flagged as being of interest to the operator. In an embodiment, the flag icon 212 is only displayed in automatic recording mode. In an embodiment, the flag icon 212 is displayed in automatic recording mode, manual recording mode, and/or hybrid recording mode.

The display 18 may also include a selectable still image icon 214 that permits capture of individual still images. The captured still image corresponds to the image 20 displayed on the display screen 18 at the time of selection of the still image icon 214. Thus, the operator can use the video laryngoscope 12 to capture a video feed of the procedure via image recording any/or any still images of interest.

The icons that appear on the display screen 18 over the camera view (e.g., icons 210, 212, 214, 216, 218) can be dragged on or off the screen according to a preference of the operator. Thus, if the operator wants a camera view that is completely un-impeded, the operator can swipe the icons away. To interact with the icons as desired, the operator may swipe the other way and drag the icons back onto the screen. In one example, the icons can be implemented as a mostly hidden menu provided on a first edge of the screen 18. Swiping on the visible portion of the menu at the first edge to an opposite second edge all the way across the screen 18 drags the previously hidden portion of the menu (with the icons) out onto the screen 18. The operator can interact with the icons as needed, then swipe from the second edge all the way to the first edge to hide the menu again.

Figure 7B:
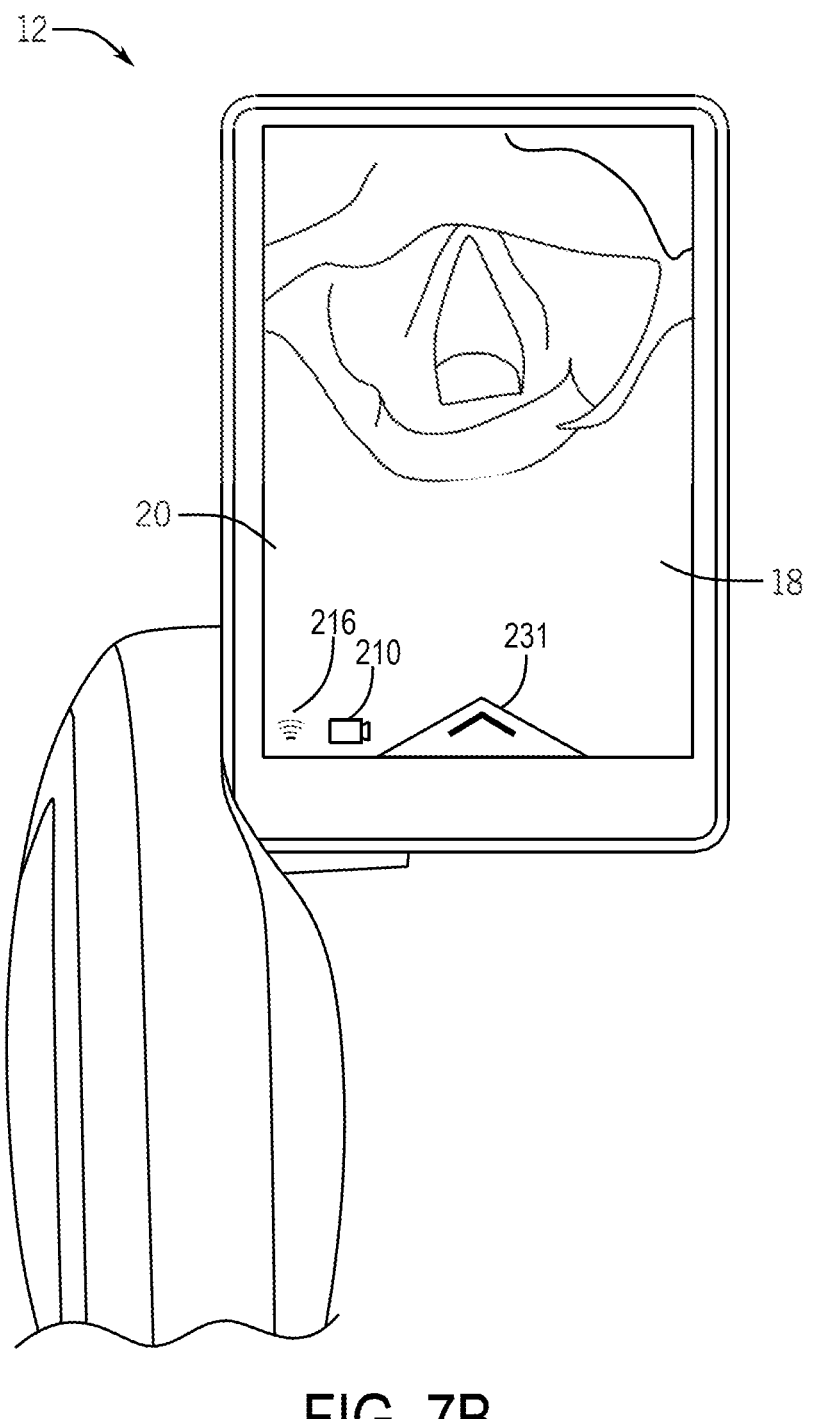

FIG. 7B depicts another example display screen 18 of a video laryngoscope 12. The example display screen 18 displays the acquired images 20 as well as recording icon 210 and wireless connectivity icon 216. In addition, the display screen 18 also includes an additional-functions indicator 231. The additional-functions indicator 231 indicates the availability of additional function or options that may be displayed on the display screen 18. When a particular interaction with the additional-functions indicator 231 is received, additional indicators are displayed. For example, a swipe input may be received that swipes the additional-functions indicator 231 upward. In other examples, a selection (or double tap) of the additional-functions indicator 231 may cause the additional-functions indicator 231 to expand and reveal additional features and functions.

Figure 7C:
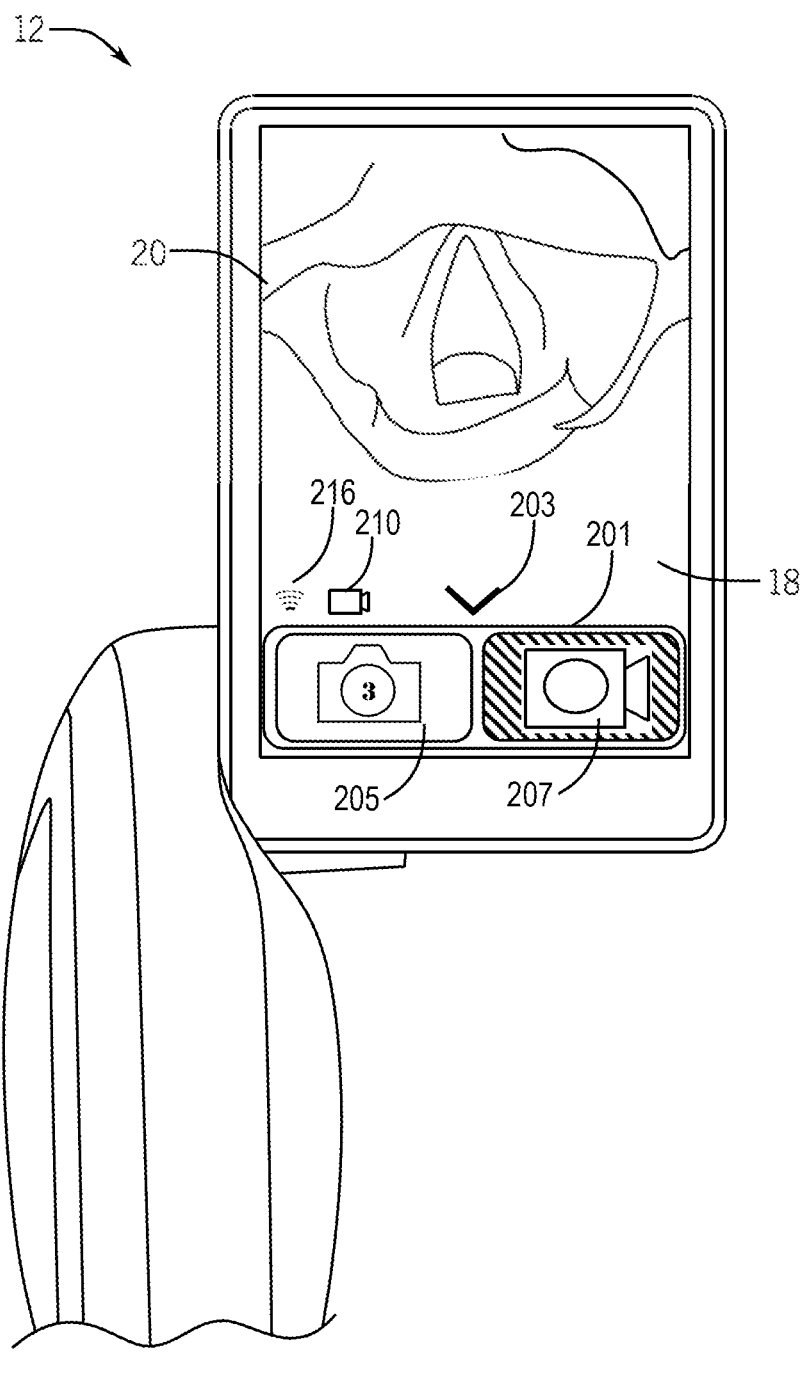

FIG. 7C depicts another example display screen 18 of a video laryngoscope 12 after the additional-functions indicator 231 has been selected (e.g., a swipe up or double tap). When the selection of the additional-functions indicator 231 is received, a container 201 of additional functions is displayed. In the example depicted, the recording icon 210 and the connectivity icon 216 continue to be be concurrently displayed when the container 201 is displayed. The recording icon 210 and the wireless connectivity icon 216 slide upwards by a distance equal to the height of the newly displayed container 201.

In addition, a collapse indicator 203 may also be displayed to allow for collapsing the container 201. For instance, if an interaction with the collapse indicator 203 is detected, the container 201 is collapsed, and the display screen returns to the state shown in FIG. 7B. The interaction with the collapse indicator 203 may be a downward swipe, double tap, or some other interaction. In some examples, when the container 201 is displayed, the container 201 may be automatically collapsed or removed from display after a timeout period (e.g., 3-5 seconds).

In the example depicted, the container 201 includes a selectable still image icon 205 and a selectable video recording icon 207. When a selection of the still image icon 205 is received, the video laryngoscope 12 captures a still image of the image displayed on the display screen 18 at the time the selectable still image icon 205 is selected. In some examples, the selectable still image icon 205 may also include a counter that indicates the number of still images that have been captured. For instance, in the example depicted, the counter indicates that three still images have been captured. If the selectable still image icon 205 were to be selected again, the counter would increment to four.

The selectable video recording icon 207 toggles whether video recording is on or off. When the selectable video recording icon 207 is selected to toggle on the video recording function, the selectable video recording icon 207 changes in appearance to indicate that video recording is occurring. For instance, in the example depicted, the selectable video recording icon 207 is filled with a different color to indicate the video-recording state. When the selectable video recording icon 207 is selected again to toggle off the video recording, the selectable video recording icon 207 changes in appearance to a different state (e.g., different color) to indicate the non-recording state. The appearance of the recording icon 210 may also change based on the selection of the selectable video recording icon 207. For instance, when the selectable video recording icon 207 is selected to toggle on the video recording function, the image recording icon 210 may be displayed in a first state. When the selectable video recording icon 207 is selected to toggle off the video recording functionality, the image recording icon 210 may be displayed in a different state or the image recording icon 210 may be removed from display.

Figure 7D:
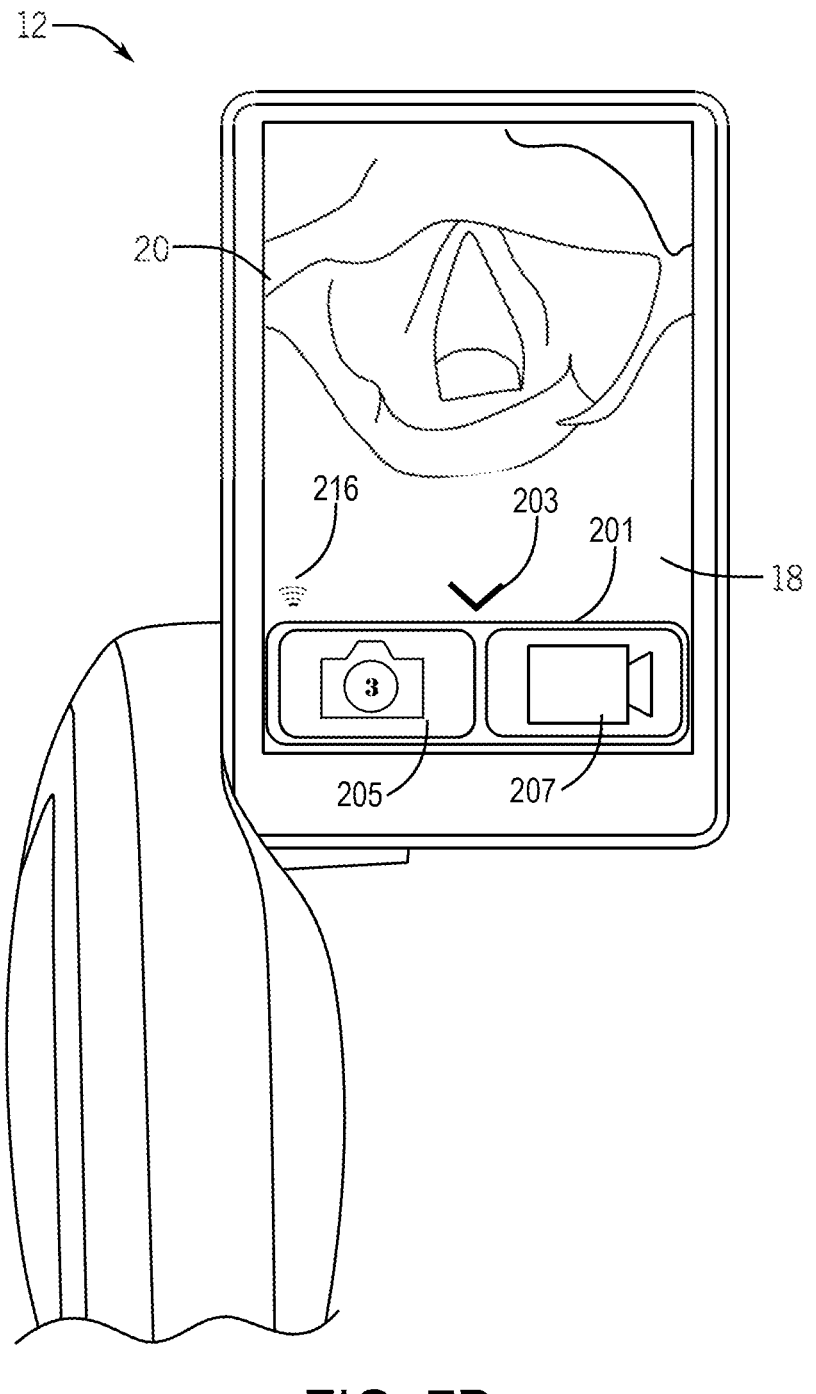

FIG. 7D depicts another example display screen 18 of a video laryngoscope 12 where the selectable video recording icon 207 has been toggled off. The appearance of the selectable video recording icon 207 changes to indicate the non-recording state, and the image recording icon 210 is also removed from the display.

By utilizing a collapsible container 201 to display the additional functionalities of the laryngoscope 12, less of the display screen 18 may be obstructed by the functions (e.g., the selectable still image icon 205 and the selectable video recording icon 207) when selection of the functions is not needed.

While the additional-functions indicator 231 and the container 201 are depicted as being positioned at the bottom edge of the display screen 18, the additional-functions indicator 231 and/or container 201 may be positioned at different edges of the screen. Advantageously, however, positioning selectable icons in the bottom and/or left-hand portion of the display screen allows the user to reach the selectable icons with his or her thumb. For example, when in use, the medical professional holds the laryngoscope 12 handle with his or her left hand, and the thumb wraps around the top of the handle near the screen. The thumb can thus reach the left and bottom portions of the screen without having to release the handle.

Figure 7E:
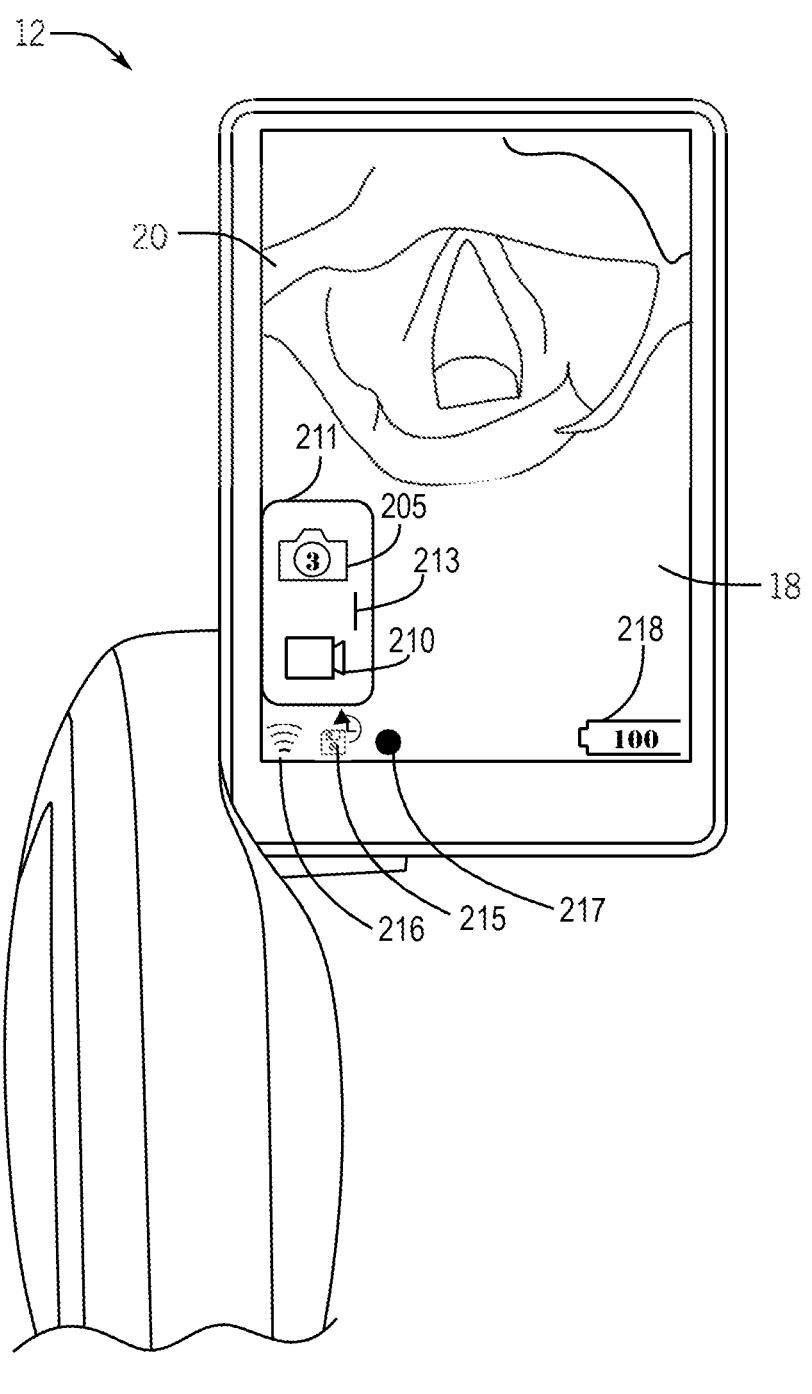

FIG. 7E depicts another example display screen 18 of a video laryngoscope 12 with a container 211 positioned on the left-hand side of the display screen 18. The container 211 includes the selectable still image icon 205 and the image recording icon 210. The image recording icon 210 may be selectable to toggle video recording on and off. The container 201 may also include a collapse indicator 213 within the container 211. Interactions with the collapse indicator allow the container 211 to be removed from the display screen 18 (e.g., the container 211 collapses into the left edge of the screen). For instance, a swipe of the collapse indicator 213 towards the edge of the screen causes the container 211 to collapse.

The display screen also includes a connectivity icon 216 and a battery level indicator 218. An automatic backup indicator 215 and another recording indicator 217 are also displayed on the display screen 18. The automatic backup indicator 215 indicates whether a backup recording is being automatically recorded (e.g., whether an automatic backup recording setting has been selected). A secondary recording icon 217 may also be included on the display 18 outside of the container 211. The secondary recording icon 217 indicates whether active video recording is occurring. For instance, secondary recording icon 217 is displayed when the image recording icon 210 is toggled to the on state. Thus, even then the container 211 is collapsed or removed from display, the secondary recording icon 217 still indicates whether active recording has been selected.

Figure 7F:
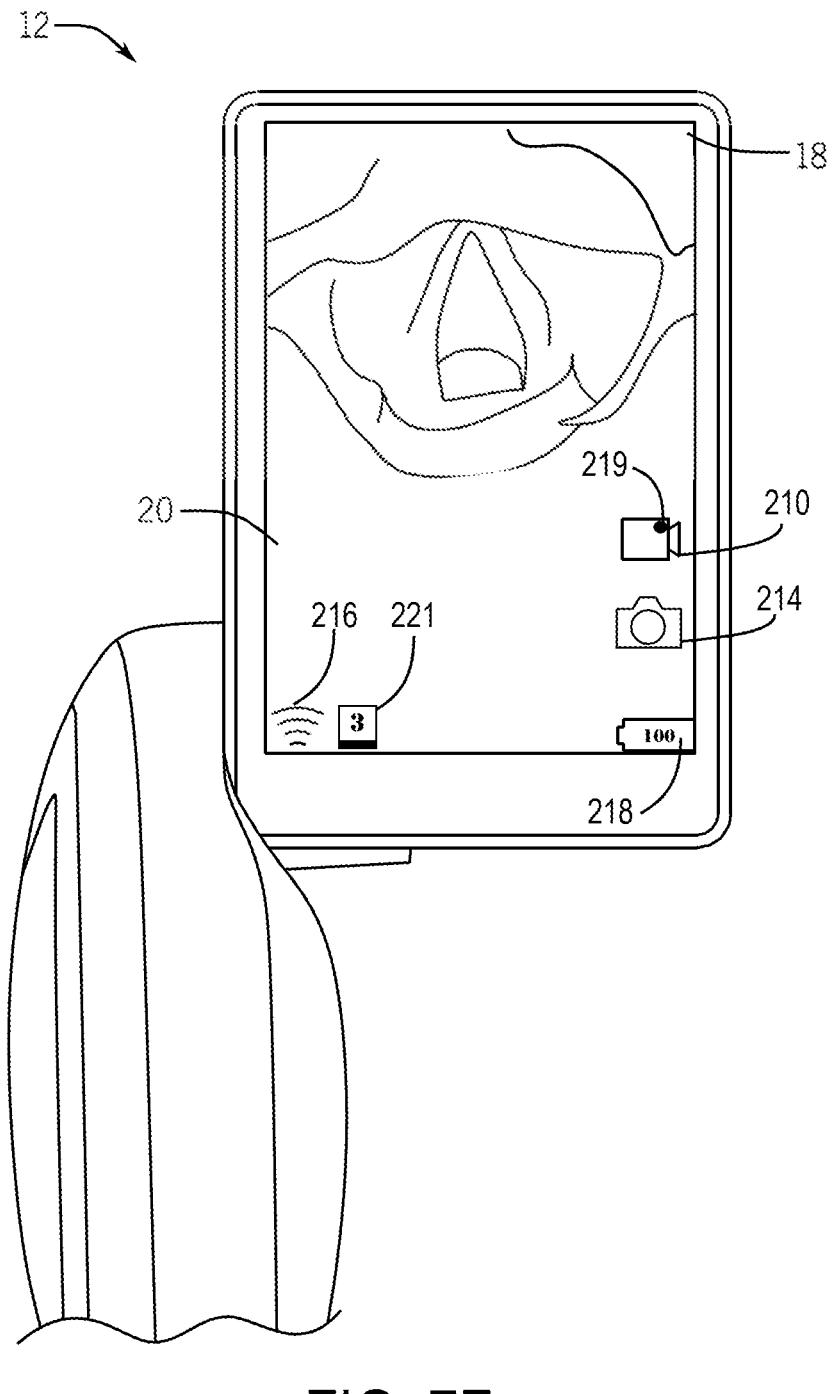

FIG. 7F depicts another example display screen 18 of a video laryngoscope 12 with another set of icons. The example display screen 18 includes the recording icon 210 and the still image icon 214. In the example depicted, the recording icon 210 and the still image icon 214 are positioned on the right edge of the display screen 18. A recording indicator 219 is displayed within the recording icon 210. When the recording icon 210 is selected to toggle on video recording, the recording indicator 219 may be displayed. When the recording icon 210 is selected to toggle off video recording, the recording indicator 219 may be removed from the display 18.

In the example depicted, the lower edge of the display screen also includes a wireless connectivity indicator 216, a battery level indicator 218, and a still image counter 221. The still image counter 221 indicates the number of still images that have been captured. For instance, in the example depicted, three still images have been captured. If the still image icon 214 were to be selected again, the number in the still image counter would increment to four.

Figure 7G:
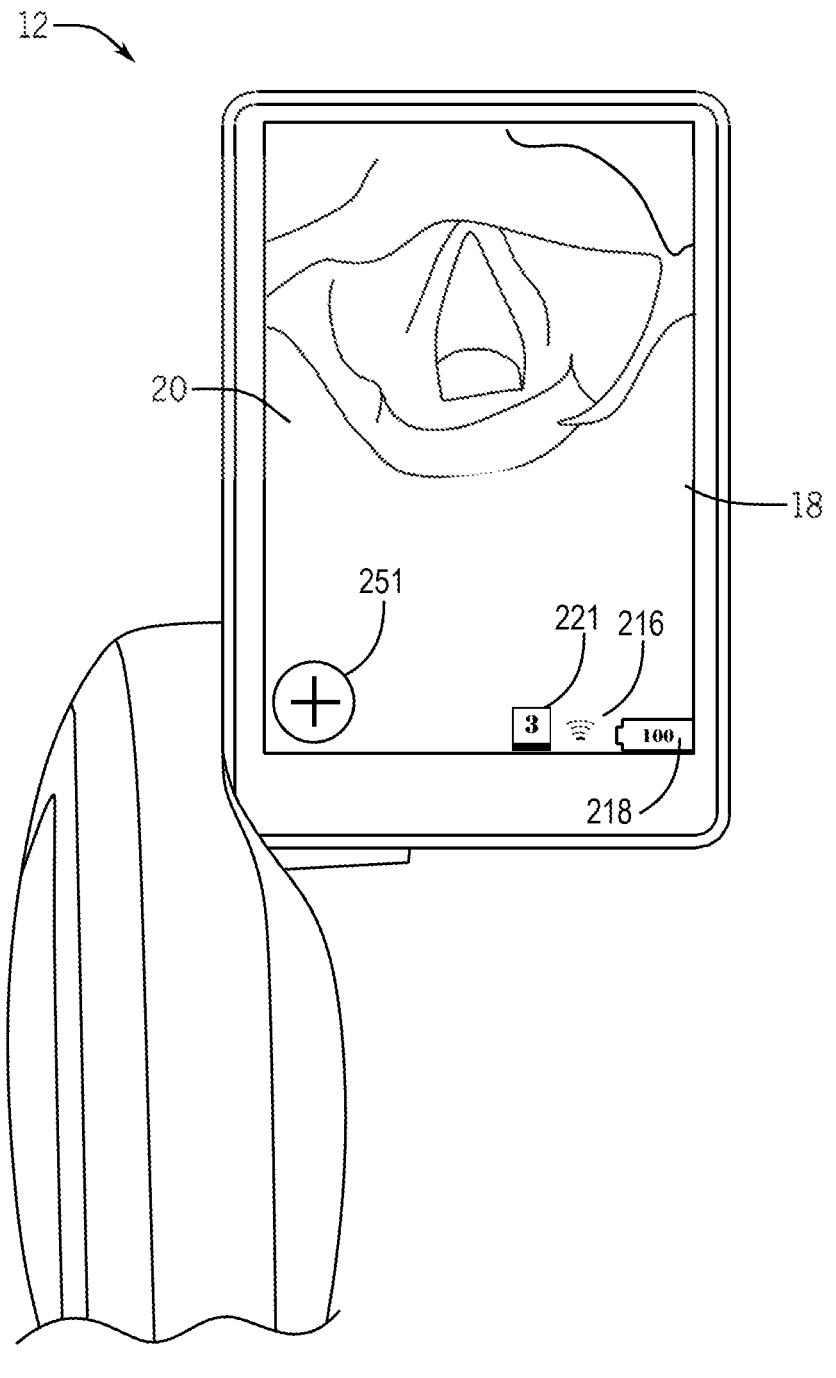

FIG. 7G depicts another example display screen 18 of a video laryngoscope 12 with a selectable expansion indicator 251. In addition to the expansion indicator 251, the still image counter 221, the connectivity indicator 216, and the still image counter 221. When the expansion indictor 251 is selected, additional functions are displayed on the display 18. In the example depicted, the expansion indicator is located in the bottom left corner (e.g., the corner located closest to the handle) such that it can be reached by a finger of the hand holding the handle.

Figure 7H:
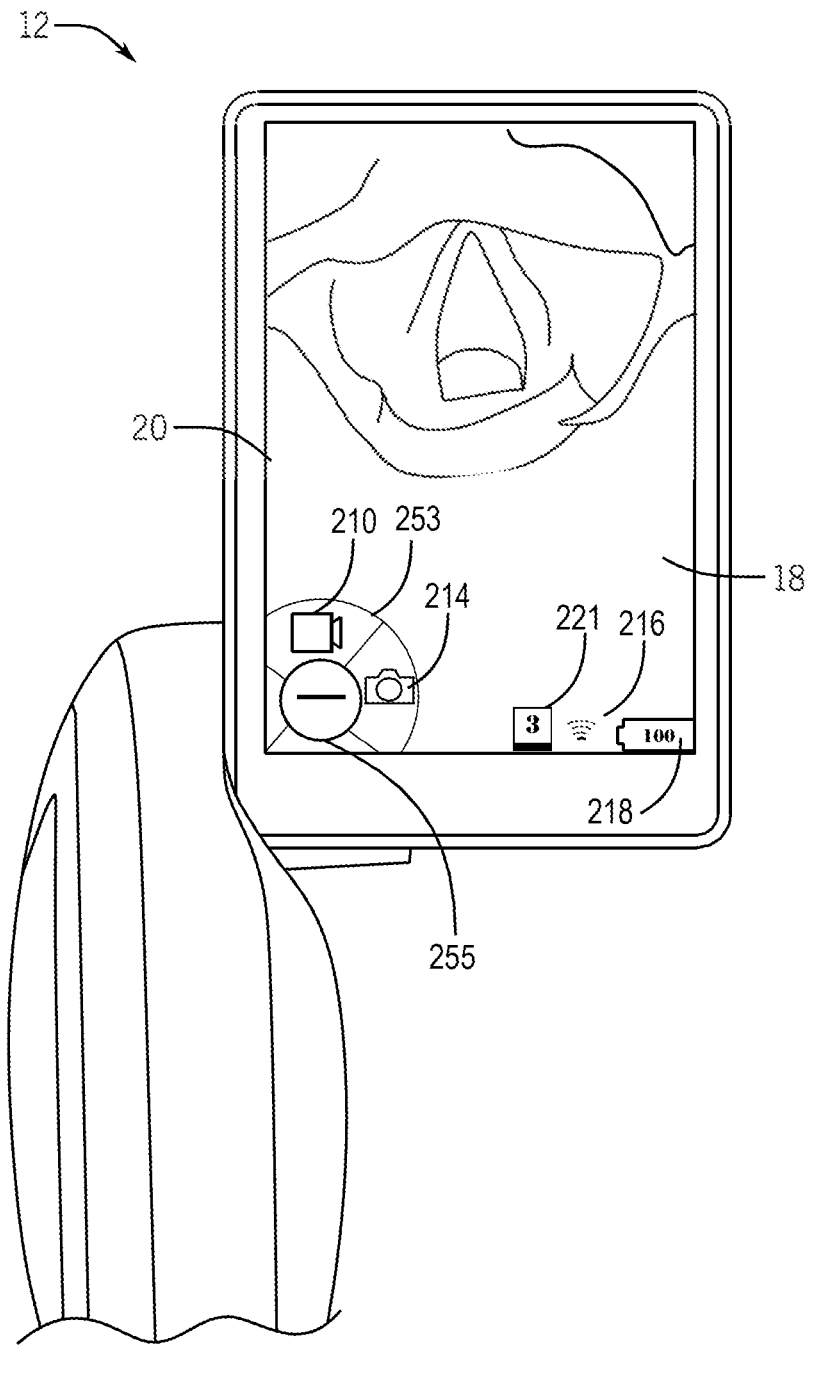

FIG. 7H depicts another example display screen 18 of a video laryngoscope 12 after the expansion indicator 251 has been selected. When the expansion indicator 251 is selected, a function ring 253 is displayed and the expansion indicator 251 changes to a collapse indicator 255. The function ring 253 includes sections with additional icons or indicators for additional functions. In the example depicted, a first section of the function ring 253 includes a video recording icon 210, and a second section of the function ring 253 includes a selectable still image icon 214. In some examples, the function ring 253 may be rotated to reveal or display additional sections of the function ring 253. The particular icons or indicators that are displayed in the respective sections of the function ring 253 may also be configurable. When the collapse indicator 255 is selected, the function ring 253 is removed from display, the expansion indicator 251 is displayed.

In addition to manual and automatic image recording modes, the video laryngoscope 12 may also include a hybrid or semi-automatic image recording mode. The hybrid image recording mode can operate with a failsafe to automatically record a backup copy of a procedure that is retained in a backup file of the video laryngoscope 12. However, the backup file is not transferred to a wireless hub 24 or moved to a main folder of the video laryngoscope unless the operator activates image recording. FIG. 8 is a process flow diagram of a hybrid recording method 220 of the video laryngoscope 12 with reference to features discussed in FIGS. 1-3 and FIGS. 7A-H, in accordance with an embodiment of the present disclosure. The video laryngoscope 12 powers on in response to a user input (block 222) and acquires images using a camera that are displayed on a display screen 18 of the video laryngoscope (block 224). In addition, the selectable image recording icon 210 is displayed. Concurrently with acquiring and displaying images, the video laryngoscope 12 also automatically initiates backup recording of the acquired images and displays the (block 226). In the hybrid recording mode, backup image recording is automatically initiated at power on, such that all images acquired while the video laryngoscope 12 is powered on in a power on cycle are automatically recorded without requiring any further user input. Optionally, the video laryngoscope 12 is paired to a wireless hub 24 (block 227).

Initially, the selectable image recording icon 210 is in the deselected or unactivated configuration. When there is no user input to select the image recording icon to activate image recording (block 228), the image recording remains in the unactivated configuration (block 230). Because the operator has not provided any image recording input, the automatically recorded images are saved to a backup file on the video laryngoscope (block 232) at the end of the power on cycle before powering off in response to a user input to power off the video laryngoscope 12 (block 236). Even when the video laryngoscope 12 is paired to a wireless hub 24 at the time the power off user input is received, the acquired images that are saved to the backup image file are not transferred (block 234) to the wireless hub 24 before the video laryngoscope 12 is powered off (block 236). Thus, the backup image file is retained only on the video laryngoscope 12 when image recording is not activated in the hybrid recording mode.

However, when a user input is received to start image recording (block 240) via selection of the selectable image recording icon 210, the selectable image recording icon is changed to an active recording configuration (block 242). The automatically recorded images are saved to a main or primary file on the video laryngoscope (block 246) in response to a user input to power off the video laryngoscope 12 (block 244). When the video laryngoscope 12 is paired to a wireless hub 24 at the time the power off user input is received, the acquired images are automatically transferred to the wireless hub 24 (block 247) before the video laryngoscope 12 is powered off (block 248). In an embodiment, the saved image file includes all acquired images from the power on cycle. That is, providing the user input to start image recording changes a status of the already-recorded backup images to a primary image file. In an embodiment, when the operator provides the user input to activate image recording, the recorded images are flagged as being of interest. In an embodiment, the saved image file includes only images acquired going forward from when the image recording is activated. Thus, the already-recorded images from the backup file that were acquired before the image recording activation are not retained. Further, the video laryngoscope 12 retains the saved image file and does not separately save a backup file in an embodiment.

Thus, in the hybrid recording mode, automatically recorded images are at least saved as a backup image file locally on the video laryngoscope 12 that can be retrieved at a subsequent point. The backup image file is not transferred to a paired wireless hub 24. However, user input can cause the video laryngoscope to retain the acquired images locally on the video laryngoscope and to transfer the acquired images to any paired wireless hubs 24.

In other examples, when the video laryngoscope 12 is recording video or images (whether automatically or through manual selection), the video laryngoscope 12 automatically transmits the recording video or image data to the connected wireless hub(s) 24 while the images are being recorded. For instance, the wireless hub 24 may be in a streaming mode and receiving the image data for display. Other wireless hubs 24 may be receiving the video data but not displaying a video stream. The wireless hubs 24 store the received data during the clinical procedure. At the end of the procedure, when the video laryngoscope 12 receives an input to power off, the video laryngoscope 12 transmits a message to all connected wireless hubs 24 to indicate whether the video data should be kept (e.g., stored) or deleted. For example, where manual recording has been selected and/or a flag input has been received, a message may be sent from the video laryngoscope 12 to the wireless hub(s) 24 indicating that the video files should be stored. In another example, where the recording is automatic and no flag input is received, the video laryngoscope 12 may send a message to the wireless hub(s) 24 to delete the video file.

Figure 9:
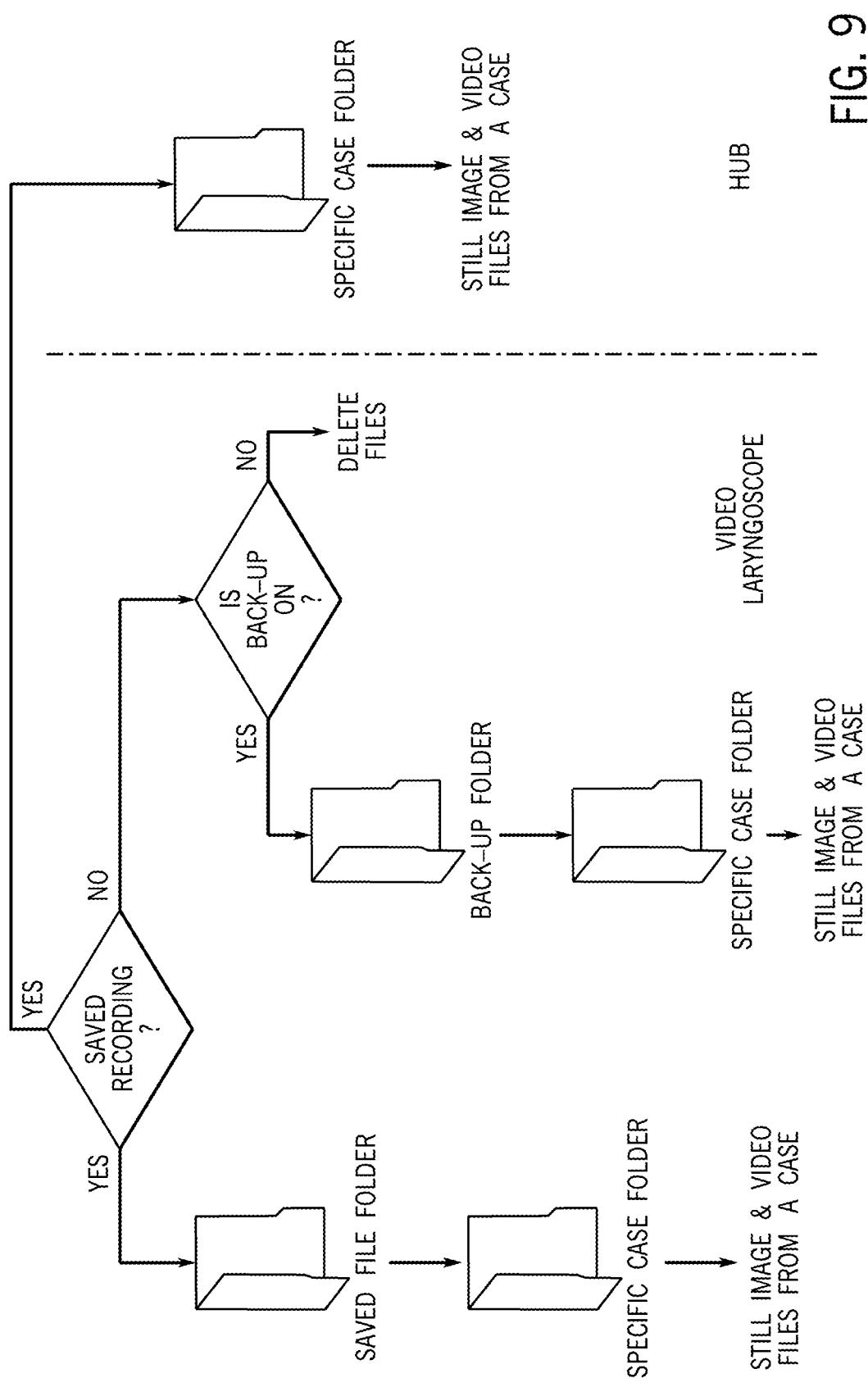
FIG. 9 is a schematic illustration of file organization of stored images in a video laryngoscope and a wireless hub, in accordance with an embodiment of the present disclosure.

FIG. 9 is a schematic illustration of a file organization flow diagram of a video laryngoscope 12 and a wireless hub 24. Whether acquired images are saved or not saved is a function of the selected recording mode of the video laryngoscope 12 and, in certain embodiments, user inputs received during operation while the images are acquired. For example, when the video laryngoscope 12 is in automatic recording mode, all acquired images are saved locally on the video laryngoscope in a saved file folder. When the video laryngoscope 12 is in manual recording mode or hybrid recording mode, images are saved to the saved file folder only when the operator provides an image recording user input while the images are being acquired. The saved file folder can include subfolders for each specific case. An individual case may be designated as all images, including video and still images, acquired during a power on cycle of the video laryngoscope 12. In an embodiment, images acquired during two different, but adjacent, power on cycles, can be grouped together in a single case. For example, the video laryngoscope 12 may group together as a single case a first power on cycle that is within 15 minutes, or 5 minutes, of a second power on cycle. Such an embodiment may group together an initial laryngoscope check with a subsequent recorded procedure from the same patient. The initial laryngoscope check may include environmental images of the patient, patient identification information or barcodes, the caregivers present, and other relevant contextual information that may be helpful when reviewing the saved procedure images.

When the video laryngoscope 12 is in hybrid recording mode, backup recording is active, and images are retained in a backup file folder on the video laryngoscope. However, backup recording is not active in manual recording mode. Thus, in manual recording mode, when no user input to activate recording is received, the acquired image files are not retained. In an embodiment, any temporary or buffered memory including any acquired image files is deleted as part of the operating instructions not to retain the images in the manual recording mode.

Saved image files can be transferred to one or more paired wireless hubs 24. The transferred files can use the same organization or file arrangement as in the video laryngoscope 12. Thus, files assigned to a specific case folder can be transferred using a same file generation or naming convention as on the locally saved image file on the video laryngoscope 12. As illustrated, when the image files are transferred, all associated image files, including video and still images, are batch transferred.

Figure 10:
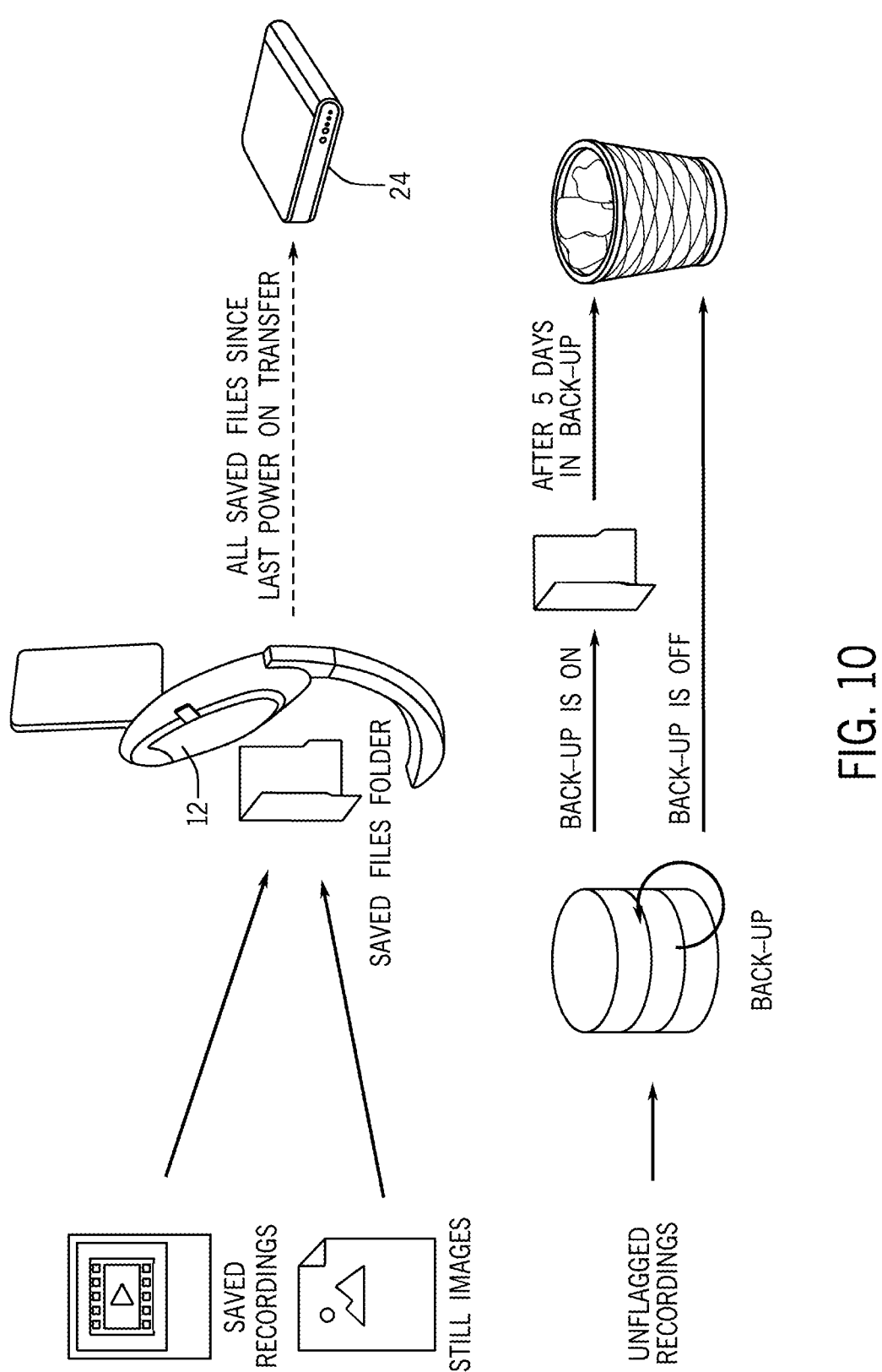
FIG. 10 is a schematic illustration of data transfer of recorded video and captured still images from a video laryngoscope to a wireless hub, in accordance with an embodiment of the present disclosure.

FIG. 10 is a schematic illustration of batch transfer of recorded images to the wireless hub 24. The transferred files can include recorded video images and still images. The video laryngoscope 12 may have retained stored files from previous procedures. However, the video laryngoscope 12 transfers files to the wirelessly paired wireless hub 24 that are recorded subsequent to the most-recent power-on. As provided herein, the data transfer may involve transmitting a copy of the images files to the paired wireless hub 24 such that the original file or files are retained on the video laryngoscope 12.

The saved recordings may be flagged or unflagged recordings. In an embodiment, some recordings may have been designated by the laryngoscope operator with a flag indicating that the acquired images are of interest. If the images are flagged, the saved files can be retained indefinitely on the video laryngoscope 12 or until the allotted memory is full. If the recordings are unflagged, and the back-up recording is on (i.e., the files were generated in hybrid recording mode), the files are retained for a period of time, such as five days, before being deleted. If the recordings are unflagged, and the back-up recording is off, any recordings can be deleted at power off.

Figure 11:
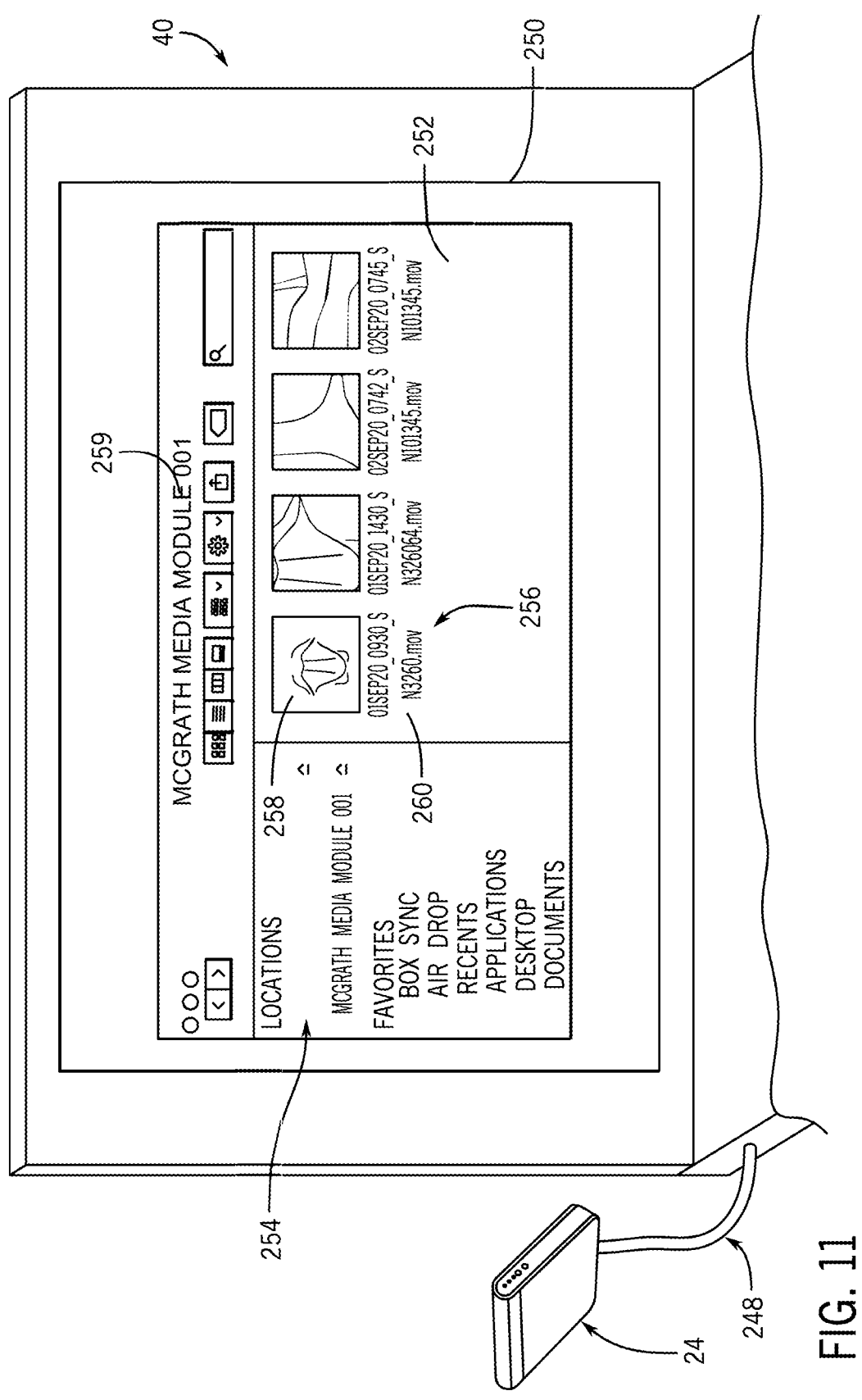
FIG. 11 is a schematic illustration of a wireless hub coupled to a computer in data review mode, in accordance with an embodiment of the present disclosure.
Figure 12:
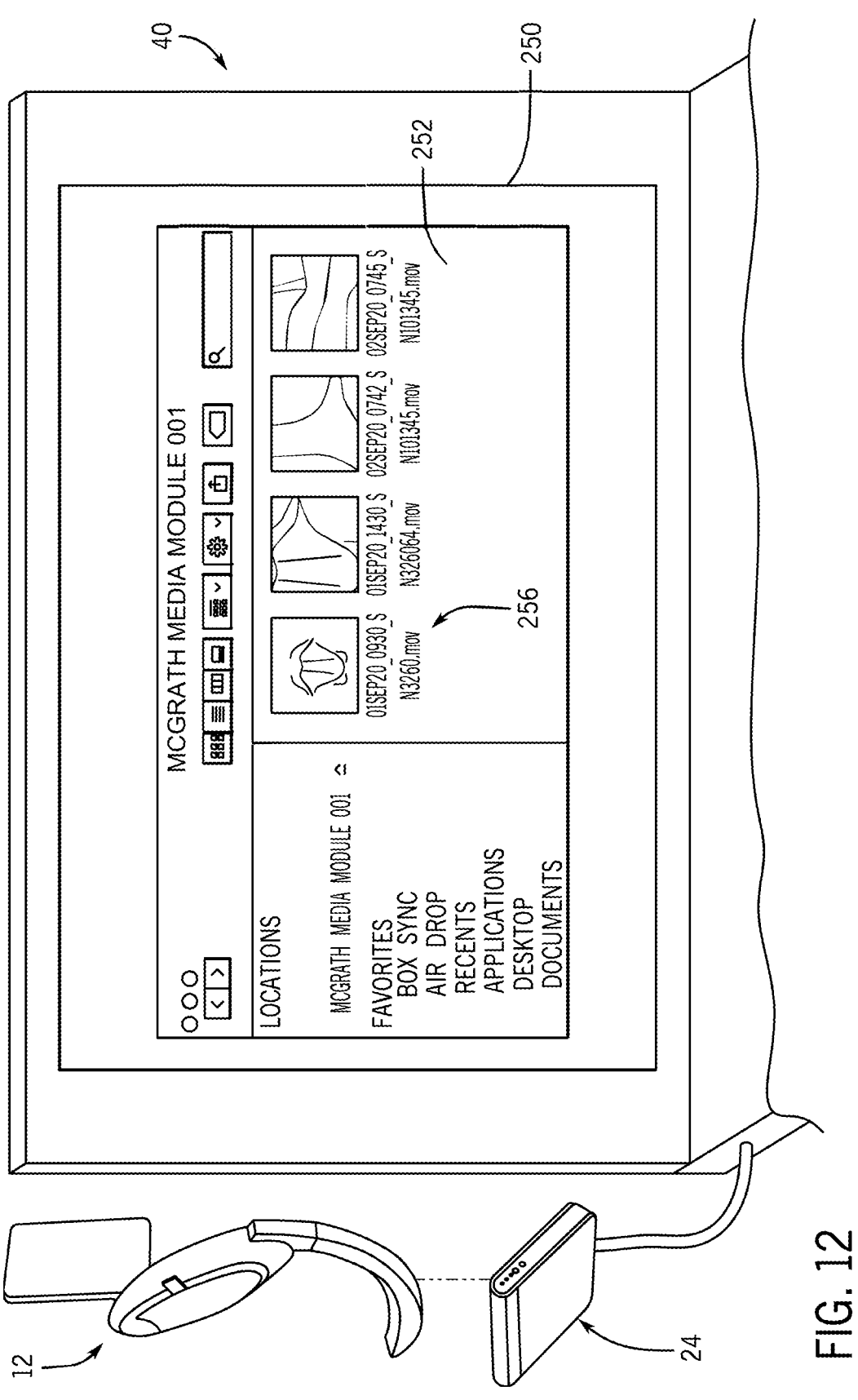
FIG. 12 shows a video laryngoscope pairing to the wireless hub in data review mode, in accordance with an embodiment of the present disclosure.
Figure 13:
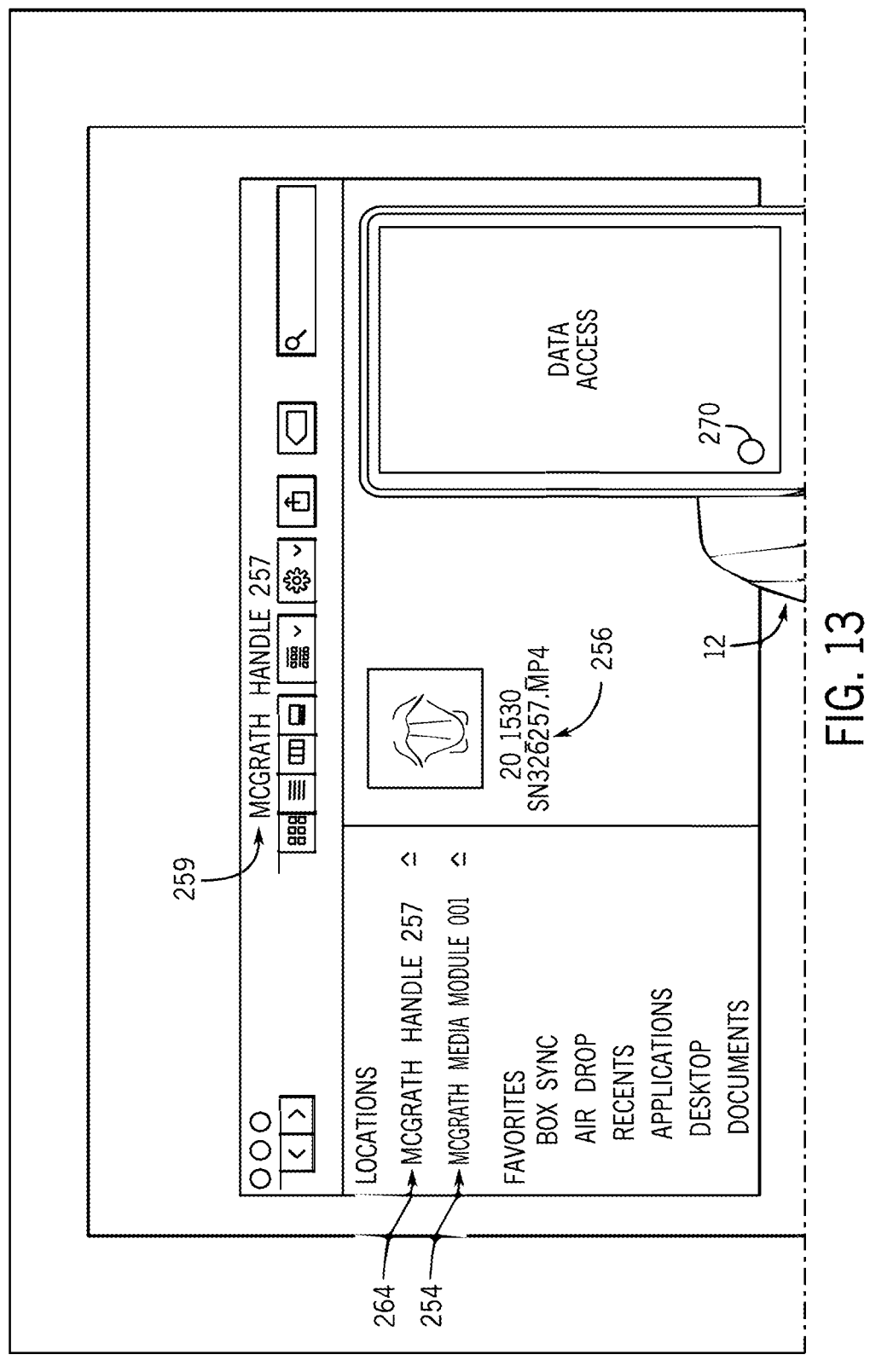
FIG. 13 shows the wireless hub operating to retrieve data from the paired video laryngoscope that is displayed on the computer in in data review mode, in accordance with an embodiment of the present disclosure.

The disclosed techniques also facilitate data retrieval and review for files stored on the video laryngoscope 12 and a wireless hub 24. FIGS. 11-13 show different data retrieval and review options for image files. FIG. 11 shows the wireless hub 24 operating in a data review mode in which stored files retained in a memory of the wireless hub 24 can be reviewed or manipulated using a personal device, such as the computer 40. Thus, the wireless hub 24 can be relatively simple or headless (e.g., with no integral display or user interface), because the user interface is provided by the computer 40. In FIG. 11, the wireless hub 24 is coupled to the computer 40, e.g., by a removable cable. However, in embodiments, the coupling may be wireless. When coupled to the computer 40, a folder 259 that includes files stored on the wireless hub 24 are reviewable on a display screen 250 of the computer 40. A user interface 252 shows a device listing 254 indicating that the coupled wireless hub 24 (e.g., the MEDIA MODULE 001) is available. The stored image files 256 on the memory of the wireless hub 24 can be reviewed on the user interface 252. Each file 256 can be shown using a thumbnail 258 and a file name 260. As discussed herein, the thumbnail 258 and the file name 260 can be selected or generated by the video laryngoscope 12 using one or more image characteristics in the image file.

FIGS. 12-13 illustrate an embodiment in which the wireless hub 24 is coupled to the computer 40 in data review mode and operates as a pass-through device to allow files retained on the video laryngoscope 12 to be viewed on the display screen 250 of the computer 40. The video laryngoscope 12 wirelessly pairs to the wireless hub 24, as shown in FIG. 12. For example, a transceiver and/or a transmitter, such as an optical transmitter, of the wireless hub 24 emits a signal that is detected by a receiver or sensor of the video laryngoscope 12 to initiated pairing. Pairing is completed via a wireless handshake between the video laryngoscope 12 and the wireless hub 24. Before the pairing, the video laryngoscope 12 is not available in the device listing 254 on the user interface 252. Once pairing is complete, as shown in FIG. 13, a listing 264 of the video laryngoscope 12 (listed as MCGRATH HANDLE 257) is visible along with the wireless hub listing 252 in the available devices, and the displayed folder 259 shows the files 256 that are stored on the video laryngoscope 12. When coupled to the wireless hub 24 that in turn is coupled to the computer 40, the video laryngoscope 12 operates in a data review mode. The initiation at the video laryngoscope 12 of the data review mode may be based on receiving signals from the wireless hub 24 indicative that the wireless hub 24 is paired to the computer 40, e.g., via a cable. The video laryngoscope 12 is powered on during the pairing to operate in the data review mode. While the video laryngoscope 12 operates in the data review mode, the camera and light source may be disabled or turned off. The display may be turned off, or may display a data access screen 268 and/or display a pairing indicator 270. The file information on the video laryngoscope 12 is communicated wirelessly to the paired wireless hub 24, which in turn passes the file information to the computer 40 to configure the user interface 252.

The computer 40 permits display of the files 256 from the video laryngoscope 12 and/or the wireless hub 24 without necessarily having the files 256 be stored on the computer 40. Thus, the file information communicated to the computer 40 may include file name, file size, file type, and thumbnail information and may, in embodiments, not include the full file. That is, the computer 40 can operate as the user interface 252 to permit a user to interact with the files 256 while the files are retained on the video laryngoscope 12 and/or the wireless hub 24. In embodiments, the interaction may include transferring (e.g., copying) the files to the computer 40 or to the wireless hub 24. The computer 40 can provide a more user-friendly interface relative to the video laryngoscope 12 for file review. Further, the wireless hub 24 may not include any file review capabilities.

Figure 14:
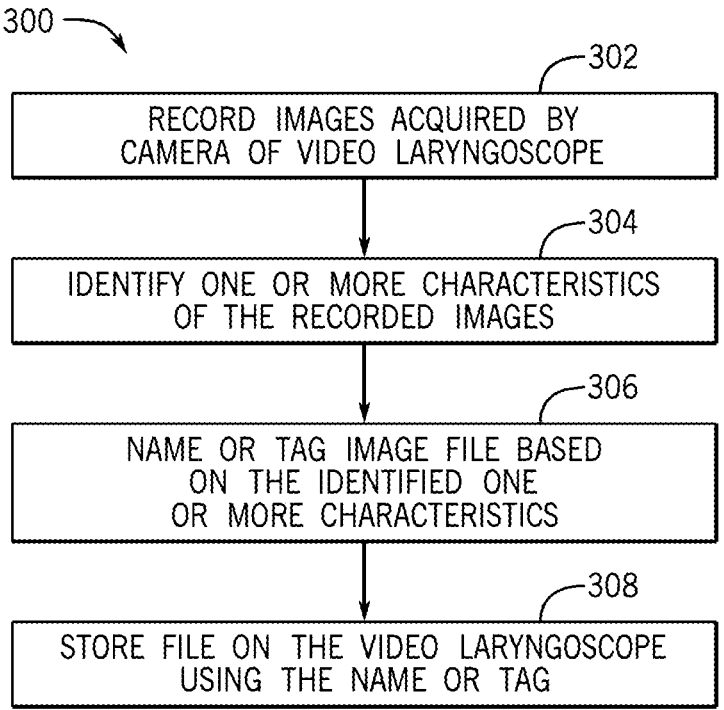
FIG. 14 is a flow diagram of a method of naming or tagging mages based on image characteristics, in accordance with an embodiment of the present disclosure.

While the computer 40 can provide a more user-friendly interface for file interaction, the video laryngoscope 12 may also organize the files according to certain file characteristics to permit a user to more readily identify particular procedures or patients. FIG. 14 is a process flow diagram of a file storage method 300 of the video laryngoscope 12 with reference to features discussed in FIGS. 1-13 and FIG. 16, in accordance with an embodiment of the present disclosure. The video laryngoscope 12 acquires images using a camera and records the images (block 302). A controller of the video laryngoscope can identify one or more characteristics of the record images (block 304), and an image file of the recorded images can be named or tagged using one or more identified characteristics of the recorded images (block 306). The file is stored on the video laryngoscope using the name (block 308).

Figure 15:
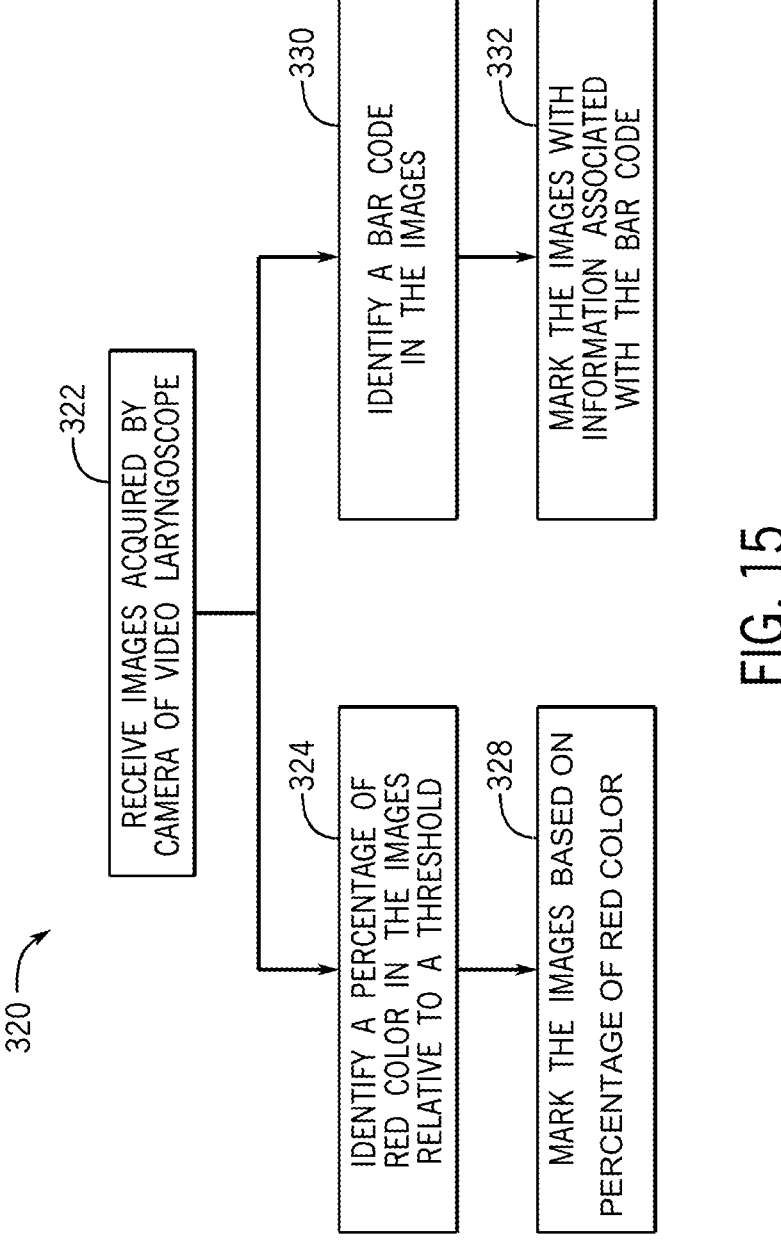
FIG. 15 is a flow diagram of a method of naming or tagging images based on image characteristics, in accordance with an embodiment of the present disclosure.

Characteristics of the images that can be used to name the file include image color or patient identifying characteristics. FIG. 15 is a process flow diagram of a file naming method 300 of the video laryngoscope 12 with reference to features discussed in FIGS. 1-14 and FIG. 16. A controller of the video laryngoscope receives the images acquired by the camera (block 322) and performs image analysis to identify characteristics. In an embodiment, image files can be analyzed for a percentage of red color (block 324). Based on an identified red percentage in the image files relative to a threshold, the file name can be marked based on the percentage of red color (block 328). For example, images that have a red percentage above a threshold characteristic of airway passages are likely to be intubations, while images having a red percentage below the threshold are unlikely to be intubations. For video files, the percentage of red color can be an average across the video file. In one example, to account for pre-intubation image capture, the image analysis can consider whether a video file has a portion of images having a red color percentage above the threshold. Thus, image files having the red color percentage above the threshold can be marked as intubations and image files having the red color percentage below the threshold can be marked as nonintubations. In certain embodiments, the analysis may be indeterminate, and the file can be marked as unknown or flagged for user review. The marking can include using "intubation" or "nonintubation" as part of the file name. In an embodiment, all files marked as intubations can be placed in an intubation subfolder.

The image analysis may also include barcode identification. For image files that include a barcode or an identifiable patient name (block 330), the barcode or patient information can be used to mark the image file (block 332) as part of the image file name. In an embodiment can be selected as the image thumbnail 258 to allow a user to quickly identify patients of interest when reviewing image files.

Figure 16:
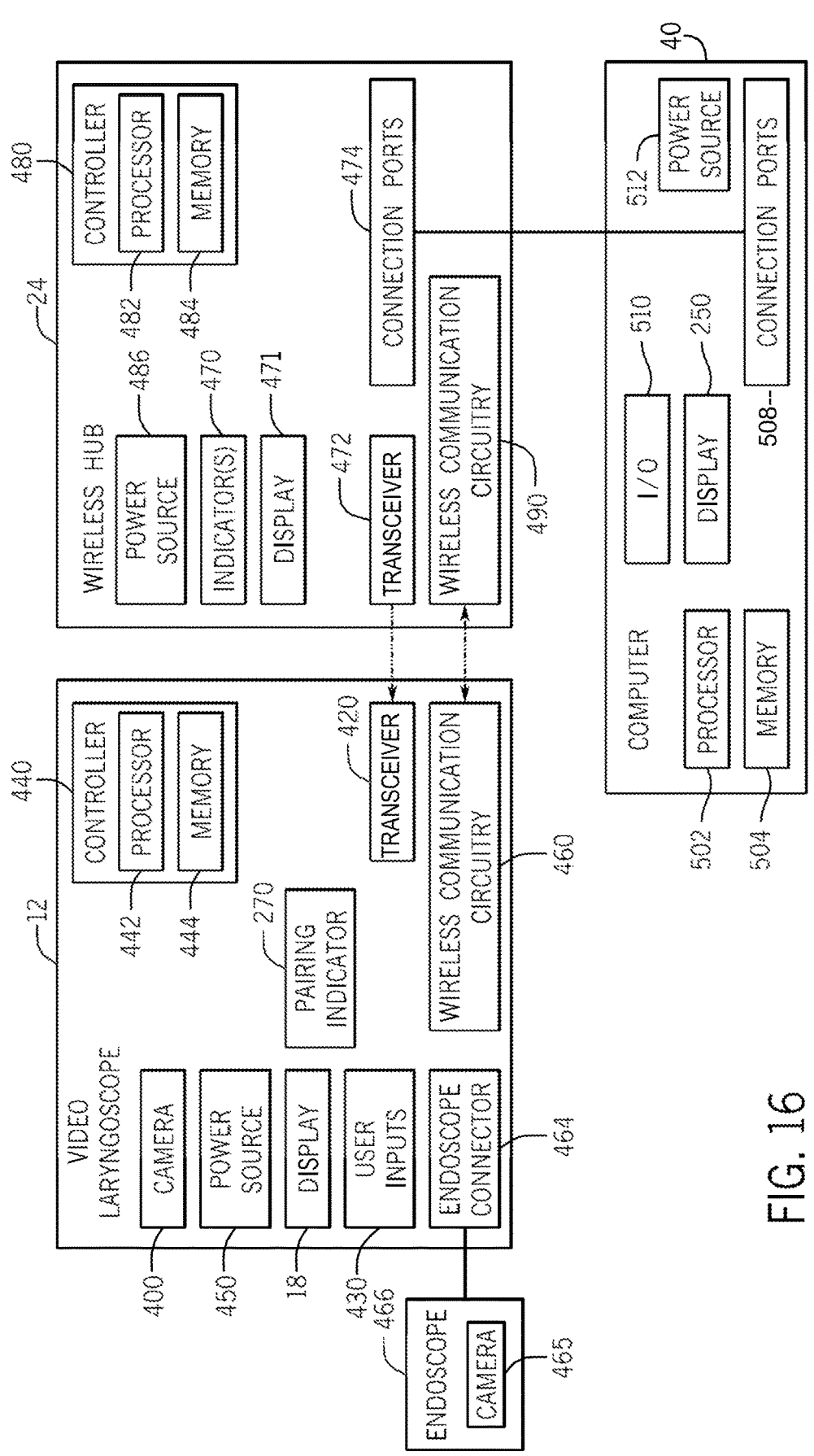
FIG. 16 is a block diagram of components of a video laryngoscope image file management system, in accordance with an embodiment of the present disclosure.

FIG. 16 is a block diagram of an embodiment of the video laryngoscope system 10. As shown, the system 10 includes the video laryngoscope 12 and at least one wireless hub 24. The video laryngoscope 12 and the wireless hub 24 may include various components that enable the system 10 to perform the techniques disclosed herein. For example, the video laryngoscope 12 may include the display screen 18, a camera 400, a sensor or transceiver 420 (such as an optical or infrared detector or sensor), and user inputs (e.g., touch sensor, power button) 430, as well as a controller 440 (e.g., electronic controller), one or more processors 442, a hardware memory 444, a power source (e.g., battery) 450, and a communication device 460, and, in embodiments, a connector 464 to an endoscope 466. The video laryngoscope 12 can receive images from the camera 465 of the endoscope 466. As discussed herein, the images 20 may be images from the laryngoscope camera 400, the endoscope camera 465, or both. The video laryngoscope 12 can provide indicators via the display 18 as well as other indicators 270 (haptic, audio, and/or visual indicators) of wireless pairing.

The wireless hub 24 may include the optical transmitter or transceiver 472, one or more indicators 470, a controller 480 (e.g., electronic controller), one or more processors 482, a hardware memory 484, a power source (e.g., battery) 486, and a communication device 490. The power sources 450, 486 may be rechargeable and/or replaceable batteries. In embodiments, the wireless hub 24 does not include any integral display.

The system 10 can include a computer 40 having a processor 502 and a memory 504. The computer includes connection ports 508 to which the wireless hub 24 can be coupled or other input/output ports 510. A power source 512 of the external display 40 can provide power to the wireless hub 24 when coupled such that the data review operating mode is powered by the computer 40.

The communication devices 460, 490 may be wireless transceivers that are configured to establish wireless communication with one another. By way of example, the communication devices may be configured to communicate using the IEEE 802.15.4 standard, and may communicate, for example, using ZigBee, WirelessHART, or MiWi protocols. Additionally or alternatively, the communication devices may be configured to communicate using the Bluetooth standard or one or more of the IEEE 802.11 standards. streaming operating mode or data transfer operating mode.

The hardware memory 444, 484, 504 may include a volatile memory, such as random access memory (RAM), and/or a nonvolatile memory, such as read-only memory (ROM). For example, the memory 444, 484, 504 may store processor-executable instructions (e.g., firmware or software) for the processors 442, 482, 502 to execute. The hardware memory 444, 484, 504 may store images 20 and instructions (e.g., software or firmware for storing the images, transmitting the images, etc.), and any other suitable data. The processor 242 of the video laryngoscope 12 may be configured to receive state information from the wireless hub 24 and perform actions consistent with the received state information to cause the wireless hub 24 to operate in an appropriate operating mode. The processor 242 of the video laryngoscope 12 may be configured to receive user inputs to record images or change a recording mode of the video laryngoscope 12 and perform actions consistent with the received user inputs to cause image recording according to the appropriate recording mode. The processor 242 of the video laryngoscope 12 may be configured to perform image analysis to name saved files of the recorded images.

The method discussed herein include various steps represented by blocks in flow diagrams. It should be noted that at least some steps may be performed as an automated procedure by one or more components of a system, such as the system 10. Although the flow diagrams may illustrates the steps in a certain sequence, it should be understood that the steps may be performed in any suitable order and certain steps may be carried out simultaneously, where appropriate. Additionally, steps may be added to or omitted from of the methods.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A video laryngoscope, comprising:
   a power switch that powers the video laryngoscope on and off in response to user input;
   a camera that acquires images while the video laryngoscope is powered on;
   a processor that operates to:
      record the acquired images;
      identify one or more image characteristics of the acquired images; and
      generate a file name for an image file of the acquired images based on the one or more identified image characteristics; and
   a memory that stores the image file, of the acquired images, with the generated file name.

2. The video laryngoscope of claim 1, comprising a display screen that displays the images acquired by the camera.

3. The video laryngoscope of claim 2, wherein the display screen comprises a graphical user icon that receives a manual input to record the acquired images.

4. The video laryngoscope of claim 1, wherein the acquired images are automatically recorded without a manual input.

5. The video laryngoscope of claim 1, further comprising communication circuitry, wherein the video laryngoscope is wirelessly paired to a wireless hub and wherein the processor operates to instruct the communication circuitry to communicate the file to the wireless hub in response to a power off user input.

6. The video laryngoscope of claim 5, wherein the file is communicated to the wireless hub with the file name.

7. The video laryngoscope of claim 1, wherein the file of the acquired images includes only images acquired between a single power on and subsequent power off cycle of the video laryngoscope.

8. The video laryngoscope of claim 1, wherein the processor associates the file with other files of acquired images acquired within a predetermined time window of acquiring the images.

9. The video laryngoscope of claim 1, wherein the one or more characteristics of the acquired images comprise a percentage of red color in the images above a threshold, wherein the processor marks the acquired images as an intubation based on the percentage.

10. The video laryngoscope of claim 1, wherein the one or more characteristics of the acquired images comprise a percentage of red color in the images below a threshold, wherein the processor marks the acquired images as not an intubation based on the percentage.

11. The video laryngoscope of claim 1, wherein the one or more characteristics of the acquired images comprise a barcode in the images, wherein the processor marks the acquired images with information associated with the barcode.

12. A video laryngoscope, comprising:
   a power switch that powers the video laryngoscope on and off in response to user input;
   a camera that acquires images while the video laryngoscope is powered on;
   a display screen that displays the images acquired by the camera;
   communication circuitry for enabling wireless communication;

a memory; and a processor that executes instructions to cause the video laryngoscope to perform operations comprising:

record the acquired images;

identify one or more image characteristics of the acquired images;

generate a file name for an image file of the acquired images based on the one or more identified image characteristics;

store the image file with the generated file name; and wirelessly communicate, via the communication circuitry, the image file with the generated file name to a wireless hub wirelessly paired with the video laryngoscope.

13. The video laryngoscope of claim 12, wherein the display screen comprises a graphical user icon that receives a manual input to record the acquired images.

14. The video laryngoscope of claim 12, wherein the acquired images are automatically recorded without a manual input after the video laryngoscope is powered on.

15. The video laryngoscope of claim 12, wherein the file of the acquired images includes only images acquired between a single power on and subsequent power off cycle of the video laryngoscope.

16. The video laryngoscope of claim 12, wherein:

the characteristic of the acquired images comprises a percentage of red color in the images;

when the percentage of red color in the images is below a threshold, the generated file name indicates a nonintubation; and when the percentage of red color in the images is above the threshold, and the generated file name indicates an intubation.

17. The video laryngoscope of claim 16, wherein the percentage of red color is an average across the images in the image file.

18. The video laryngoscope of claim 12, wherein the image characteristics include both image color and patient identifying characteristics.

19. The video laryngoscope of claim 12, wherein the operations further comprise: select an image thumbnail for the image file based on the image characteristics.

20. A video laryngoscope, comprising:

a power switch that powers the video laryngoscope on and off in response to user input;

a camera that acquires images while the video laryngoscope is powered on;

a display screen that displays the images acquired by the camera;

communication circuitry for enabling wireless communication;

a memory; and a processor that executes instructions to cause the video laryngoscope to perform operations comprising:

based on receiving a power on indication from the power switch, automatically recording the acquired images;

identify one or more image characteristics of the acquired images;

generate a name for an image file of the acquired images based on the one or more identified image characteristics;

store the image file with the generated name;

receive a power off input via the power switch; and in response to receiving the power off input, wirelessly communicate, via the communication circuitry, the image file with the generated name to a wireless hub wirelessly paired with the video laryngoscope.

* * * * *